(12) United States Patent
Hammer et al.

(10) Patent No.: US 11,518,977 B2
(45) Date of Patent: *Dec. 6, 2022

(54) MODIFIED BIOLOGICAL CONTROL AGENTS AND THEIR USES

(71) Applicant: AgBiome, Inc., Research Triangle Park, NC (US)

(72) Inventors: Philip E. Hammer, Cary, NC (US); Janice C. Jones, Apex, NC (US); Michael G. Koziel, Raleigh, NC (US); Scott Joseph Uknes, Apex, NC (US)

(73) Assignee: AgBiome, Inc., Durham, NC (US)

( * ) Notice: Subject to any disclaimer, the term of this patent is extended or adjusted under 35 U.S.C. 154(b) by 297 days.

This patent is subject to a terminal disclaimer.

(21) Appl. No.: 16/725,667

(22) Filed: Dec. 23, 2019

(65) Prior Publication Data

US 2020/0146299 A1 May 14, 2020

Related U.S. Application Data

(63) Continuation of application No. 15/788,370, filed on Oct. 19, 2017, now Pat. No. 10,575,529, which is a continuation of application No. 14/808,473, filed on Jul. 24, 2015, now Pat. No. 9,877,486, which is a continuation-in-part of application No. 14/608,940, filed on Jan. 29, 2015, now Pat. No. 10,508,280.

(60) Provisional application No. 62/104,122, filed on Jan. 16, 2015, provisional application No. 61/933,954, filed on Jan. 31, 2014.

(51) Int. Cl.
| | |
|---|---|
| *A01N 25/00* | (2006.01) |
| *C12N 1/20* | (2006.01) |
| *A01N 57/20* | (2006.01) |
| *C12N 1/36* | (2006.01) |
| *A01N 63/27* | (2020.01) |
| *A01N 43/653* | (2006.01) |
| *A01N 43/54* | (2006.01) |
| *A01N 43/40* | (2006.01) |
| *A01N 25/14* | (2006.01) |
| *C12N 9/10* | (2006.01) |
| *C12N 15/78* | (2006.01) |
| *A01N 37/34* | (2006.01) |
| *A01N 25/08* | (2006.01) |
| *A01N 37/22* | (2006.01) |
| *C12R 1/39* | (2006.01) |

(52) U.S. Cl.
CPC ............ *C12N 1/205* (2021.05); *A01N 25/00* (2013.01); *A01N 25/08* (2013.01); *A01N 25/14* (2013.01); *A01N 37/22* (2013.01); *A01N 37/34* (2013.01); *A01N 43/40* (2013.01); *A01N 43/54* (2013.01); *A01N 43/653* (2013.01); *A01N 57/20* (2013.01); *A01N 63/27* (2020.01); *C12N 1/36* (2013.01); *C12N 9/1092* (2013.01); *C12N 15/78* (2013.01); *C12Y 205/01019* (2013.01); *C12R 2001/39* (2021.05)

(58) Field of Classification Search
CPC ........ C12N 1/205; C12N 1/36; C12N 9/1092; C12N 15/78; C12Y 205/01019; C12Y 2001/39
See application file for complete search history.

(56) References Cited

U.S. PATENT DOCUMENTS

| | | | |
|---|---|---|---|
| 4,094,097 | A | 6/1978 | Alexander et al. |
| 4,306,027 | A | 12/1981 | Alexander et al. |
| 4,647,533 | A | 3/1987 | Weller et al. |
| 4,798,723 | A | 1/1989 | Dart et al. |
| 4,975,277 | A | 12/1990 | Janisiewicz et al. |

(Continued)

FOREIGN PATENT DOCUMENTS

| | | |
|---|---|---|
| CN | 1531594 | 9/2004 |
| CN | 1636065 | 7/2005 |

(Continued)

OTHER PUBLICATIONS

Ahemad et al., "Toxicological assessment of selective pesticides towards plant growth promoting activities of phosphate solubilizing Pseudomonas aeruginosa," Acta Microbiologial et Immunologica Hungarica, Sep. 2011, 58(3):169-187.

(Continued)

*Primary Examiner* — Ali Soroush
(74) *Attorney, Agent, or Firm* — Womble Bond Dickinson (US) LLP

(57) ABSTRACT

Methods for improving the ability of a population of biological agents to compete and survive in a field setting are provided. By improving the population of biological agents, the modified population of agents is able to grow, compete with other microbial strains and fungi, and provide protection for plants from pathogens. In particular, modified biological agents and modified populations of such agents that are herbicide tolerant or resistant are selected or engineered. In this manner, the protection from disease-causing agents is enhanced. Such modified populations of biological agents can be added to soils to prevent fungal pathogens and the diseases they cause promoting plant growth. Therefore, the present invention is useful for enhancing the competitiveness of modified biological agents particularly over other microbial agents which are not herbicide resistant. Compositions of the invention include selected or engineered herbicide resistant biological agents and modified populations of biocontrol agents. These modified biological agents can be used as an inoculant or as a seed coating for plants and seeds.

9 Claims, 1 Drawing Sheet

(56) References Cited

U.S. PATENT DOCUMENTS

| | | | |
|---|---|---|---|
| 5,264,210 A | 11/1993 | Novitski et al. |
| 5,348,742 A | 9/1994 | Howell et al. |
| 5,496,547 A | 3/1996 | Lam et al. |
| 5,639,949 A | 6/1997 | Ligon et al. |
| 5,643,774 A | 7/1997 | Ligon et al. |
| 5,662,898 A | 9/1997 | Ligon et al. |
| 5,670,350 A | 9/1997 | Gaffney et al. |
| 5,679,560 A | 10/1997 | Ligon et al. |
| 5,686,282 A | 11/1997 | Lam et al. |
| 5,686,283 A | 11/1997 | Gaffney et al. |
| 5,698,425 A | 12/1997 | Ligon et al. |
| 5,710,031 A | 1/1998 | Gaffney et al. |
| 5,723,759 A | 3/1998 | Ligon et al. |
| 5,756,087 A | 5/1998 | Gaffney et al. |
| 5,780,080 A | 7/1998 | Leifert et al. |
| 5,817,502 A | 10/1998 | Ligon et al. |
| 5,891,688 A | 4/1999 | Gaffney et al. |
| 5,955,348 A | 9/1999 | Ligon et al. |
| 6,017,752 A | 1/2000 | Janisiewicz et al. |
| 6,077,505 A | 6/2000 | Parke et al. |
| 6,117,670 A | 9/2000 | Ligon et al. |
| 6,232,270 B1 | 5/2001 | Branly et al. |
| 6,242,498 B1 | 6/2001 | Curtze et al. |
| 7,150,877 B2 | 12/2006 | Nuninger et al. |
| 8,748,345 B2 | 6/2014 | Hodge |
| 9,089,139 B2 | 7/2015 | Sakai et al. |
| 9,149,044 B2 | 10/2015 | Pedersen et al. |
| 9,635,861 B2 | 5/2017 | Hammer et al. |
| 9,668,485 B2 | 6/2017 | Hammer et al. |
| 9,675,081 B2 | 6/2017 | Hammer et al. |
| 9,686,998 B2 | 6/2017 | Hammer et al. |
| 9,795,144 B2 | 10/2017 | Hammer et al. |
| 9,795,145 B2 | 10/2017 | Hammer et al. |
| 9,795,146 B2 | 10/2017 | Hammer et al. |
| 9,877,486 B2 | 1/2018 | Hammer et al. |
| 10,575,529 B2 * | 3/2020 | Hammer .............. C12N 1/205 |
| 2001/0046492 A1 | 11/2001 | Nuninger et al. |
| 2002/0015988 A1 | 2/2002 | Enzmann et al. |
| 2005/0164999 A1 | 7/2005 | Foor et al. |
| 2008/0163392 A1 | 7/2008 | Zink et al. |
| 2008/0287297 A1 | 11/2008 | Scholer et al. |
| 2011/0257009 A1 | 10/2011 | Seitz et al. |
| 2011/0301030 A1 | 12/2011 | Pujos et al. |
| 2012/0252672 A1 | 10/2012 | Kang et al. |
| 2012/0266332 A1 | 10/2012 | Kuykendall |
| 2015/0327557 A1 | 11/2015 | Hammer et al. |
| 2016/0345585 A1 | 12/2016 | Jones et al. |
| 2016/0345586 A1 | 12/2016 | Jones et al. |
| 2016/0353744 A1 | 12/2016 | Jones et al. |
| 2016/0353745 A1 | 12/2016 | Jones et al. |
| 2017/0150718 A1 | 6/2017 | Hammer et al. |
| 2017/0150726 A1 | 6/2017 | Hammer et al. |
| 2017/0150727 A1 | 6/2017 | Hammer et al. |
| 2017/0273310 A1 | 9/2017 | Hammer et al. |
| 2018/0116227 A1 | 5/2018 | Hammer et al. |

FOREIGN PATENT DOCUMENTS

| | | |
|---|---|---|
| CN | 1695457 | 11/2005 |
| CN | 101953377 | 1/2011 |
| CN | 102108360 | 6/2011 |
| CN | 103509740 | 1/2014 |
| EP | 0466133 | 1/1992 |
| EP | 1018545 | 7/2000 |
| EP | 3099172 | 12/2016 |
| ID | 2017-07106 | 7/2017 |
| JP | H05-310521 | 11/1993 |
| JP | 7126111 | 5/1995 |
| JP | H08-503223 | 4/1996 |
| JP | H10-502803 | 3/1998 |
| JP | 2001-247423 | 9/2001 |
| JP | 2005-289944 | 10/2005 |
| JP | 2006-506345 | 2/2006 |
| JP | 2012-515548 | 7/2012 |
| JP | 2012-521390 | 9/2012 |
| JP | 2013-014573 | 1/2013 |
| JP | 2013-060401 | 4/2013 |
| JP | 2013-523856 | 6/2013 |
| JP | 2017-505769 | 2/2017 |
| JP | 2018-042562 | 3/2018 |
| KR | 10-2011-0132461 | 12/2011 |
| RU | 2154943 | 8/2000 |
| VN | 50681 | 2/2017 |
| WO | WO 1991/003161 | 3/1991 |
| WO | WO 1994/010845 | 5/1994 |
| WO | WO 1995/020040 | 7/1995 |
| WO | WO 1995/28085 | 10/1995 |
| WO | WO 1998/050422 | 11/1998 |
| WO | WO 1999/16859 | 4/1999 |
| WO | WO 1999/026479 | 6/1999 |
| WO | WO 2002/087343 | 11/2002 |
| WO | WO 2007/064828 | 6/2007 |
| WO | WO 2007/149817 | 12/2007 |
| WO | WO 2010/108973 | 9/2010 |
| WO | WO 2011/022435 | 2/2011 |
| WO | WO 2011/029002 | 3/2011 |
| WO | WO 2011/128297 | 10/2011 |
| WO | WO 2011/151819 | 12/2011 |
| WO | WO 2012/140212 | 10/2012 |
| WO | WO 2013/150422 | 10/2013 |
| WO | WO 2014/145883 | 9/2014 |
| WO | WO 2015/116838 | 8/2015 |
| WO | WO 2017/019448 | 2/2017 |

OTHER PUBLICATIONS

Ahemad et al., "Evaluation of plant-growth-promoting activities of rhizobacterium *Pseudomonas putida* under herbicide stress," Annals of Microbiology, 2012, 62(4):1531-1540.

Anand et al., "Management of Cucumber (*Cucumis sativus* L.) Mildews through Azoxystrobin-Tolerant Pseudomonas Fluorescens," J Agric Sci and Technol, 2009, 11:211-226.

Baird et al., "Evaluation of Seed Treatments on Shrunken-2 Sweet Corn," Aug. 1994, Plant Disease, 78(8):817-821.

Burr et al., "Increased Potato Yields by Treatment of Seedpieces with Specific Strains of *Pseudomonas fluorescens* and *P. putida*," 1978, Phytopathology, 68:1377-1383.

Chan et al., "Effects of Paraquat and Glyphosate on Growth, Respiration, and Enzyme Activity of Aquatic Bacteria," 1986, Bull Environ Contam Toxicol, 36:52-59.

Chennakesavulu et al., "Evaluation of different fungicides and their compatibility with *Pseudomonas fluorescens* in the control of redgram wilt incited by *Fusarium udum*," Journal of Biological Control, 2013, 27(4):354-361.

Chin-A-Woeng et al., "Biocontrol by Phenazine-1-carboxamide-Producing *Pseudomonas chlororaphis* PCL 1391 of Tomato Root Rot Caused by *Fusarium oxysporum* f. sp. radicis-lycopersici," 1998, MPMI, 11(11):1069-1077.

Janda et al., "16S rRNA Gene Sequencing for Bacterial Identification in the Diagnostic Laboratory: Pluses, Perils, and Pitfalls," 2007, J Clin Microbiol, 45(9):2761-2764.

Kishore et al., "Management of late leaf spot of groundnut (*Arachis hypogaea*) with chlorothalonil-tolerant isolates of *Pseudomonas aeruginosa*," Plant Pathology, 2005, 54:401-408.

Kristek et al., "Effect of bacterium *Pseudomonas fluorescens* and low fungicide dose seed treatments on parasite fungus *Aphanomyces cochlioides* and sugar beet yield and quality," Plant Soil Environmen, 2006, 52(7):314-320.

Liang et al., "A single residue mutation of 5-enoylpyruvylshikimate-3-phosphate synthase in Pseudomonas stutzeri enhances resistance to the herbicide glyphosate," 2008, Biotechnol Lett, 30:1397-1401.

Mohiddin et al., "Tolerance of fungal and bacterial biocontrol agents to six pesticides commonly used in the control of soil borne plant pathogens," Glob J Pest Dis Crop Prot, Nov. 2013, 1(1):001-004.

Nakorchevsky et al., "Detection of Low Level Mixed Chimerism Using High Throughput SNP Genotyping," J Blood Disord Transfus, 2016, 7(1):8 pp.

Sarma et al., "Application of inorganic carrier-based formulations of fluorescent pseudo monads and *Piriformospora indica* on tomato plants and evaluation of their efficacy," 2011, Journal of Applied Microbiology, 111:456-466.

(56) References Cited

OTHER PUBLICATIONS

Schulz et al., "Differential sensivity of bacterial 5-enolpyruvylshikimate-3-phosphate synthases to the herbicide glyphosate," FEMS Microbiology Letters, 1985, 28:297-301.

Shweta et al., "Beneficial Effects of Fluorescent Pseudomanads on Seed Germination, Growth Promotion, and Suppression of Charcoal Rot in Groundnut (*Arachis hypogea* L.)," 2008, J Microbiol Biotechnol, 18(9):1578-1583.

Silby et al., "*Pseudomonas* genomes: diverse and adaptable," 2011, FEMS Microbiol Rev, 35:652-680.

Stockwell et al., "Using *Pseudomonas* spp. for Integrated Biological Control," Phytopathology, 2007, 97(2):244-249.

Sun et al., "Novel AroA with High Tolerance to Glyphosate, Encoded by a Gene of *Pseudomonas putida* 4G-1 Isolated from an Extremely Polluted Environment in China," Aug. 2005, Applied and Environmental Microbiology, 71(8):4771-4776.

"Tebuconazole 3.6 Select," United States Environmental Protection Agency, 2013, 54 pages.

Yildiz et al., "The Effects of Biological and Chemical Treatment on Gray Mold Disease in Tomatoes Grown under Greenhouse Conditions," Turk J Agric For, 2007, 31:319-325.

International Preliminary Report on Patentability dated Feb. 8, 2018, in PCT/US2016/043330.

International Search Report dated Apr. 10, 2015, in PCT/US2015/013564.

International Search Report dated Sep. 19, 2016, in PCT/US2016/043330.

Lang et al., "Expression, Characterization, and Site-Directed Mutation of a Multiple Herbicide-Resistant Acetohydroxyacid Synthase (rAHAS) from *Pseudomonas* sp. Lm10," Curr Microbiol., 2011, 63:145-150.

\* cited by examiner

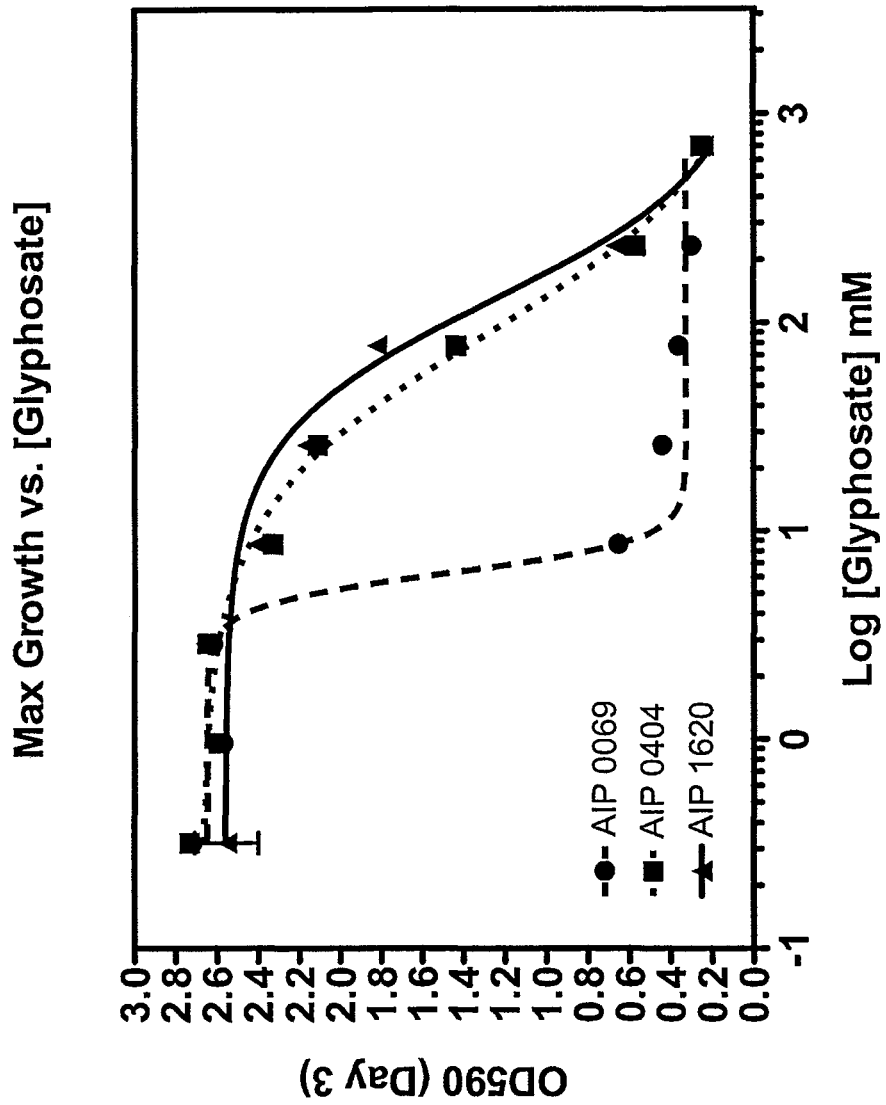

MODIFIED BIOLOGICAL CONTROL AGENTS AND THEIR USES

CROSS REFERENCE TO RELATED APPLICATION

This application is a Continuation application of U.S. application Ser. No. 15/788,370, filed Oct. 19, 2017, which is a Continuation of U.S. application Ser. No. 14/808,473, filed Jul. 24, 2015, which is a Continuation-in-part of U.S. application Ser. No. 14/608,940, filed Jan. 29, 2015, which claims the benefit of U.S. Provisional Application Ser. No. 61/933,954, filed Jan. 31, 2014, and U.S. Provisional Application Ser. No. 62/104,122, filed Jan. 16, 2015; the contents of each application recited are herein incorporated by reference in their entirety.

FIELD OF THE INVENTION

The invention relates to modified biocontrol agents and populations that have improved properties.

BACKGROUND

Plant diseases and pests need to be controlled to maintain the quality and quantity of food, feed, and fiber produced by growers around the world. Plant diseases are mainly caused by fungi, bacteria, viruses and nematodes. Plant pests include chewing, sucking and piercing insects from the Lepdoptera, Coleoptera, and Hemiptera, among others. Chemical pesticides are widely used in farming to protect crops from such pests and diseases. These chemical products fight crop pests, diseases, and weeds, resulting in improved yield. Without crop protection and pest control, food production and the quality of food produced would decline. However, the use of chemical pesticides does impose a level of risk as many have properties that can endanger health and the environment if not used properly.

A problem with the continued use of pesticides, herbicides, or other crop protection chemicals is the development of resistance to the control agent. Pesticide resistance is the decreased susceptibility of a pest population to a control agent at doses that once killed most individuals of the species. Therefore, new products are needed with different modes of action to aid in resistance management.

It has long been known that phylogenetically diverse microorganisms can act as natural antagonists of various plant pathogens and pests. Interactions between plant hosts and microorganisms that lead to biocontrol can include antibiosis, competition, induction of host resistance, and predation. Screening and testing isolates have yielded a number of candidates for commercialization. Microbial biopesticides represent an important option for the management of plant diseases and pests. There is a need for biological control agents that are able to compete in field conditions particularly in the presence of herbicides and fungicides that are commonly used in commercial farming and can have antibiotic effects on microorganisms.

SUMMARY

Compositions and methods for improving the ability of a population of biological agents or biocontrol agents to compete and survive in a field setting are provided. By improving the population of biological agents, the modified population of agents is able to grow, compete with other microbial strains and fungi, and provide protection for plants from pathogens. In addition, modified biological control agents promote plant growth and yield. In particular, modified biological agents and modified populations of such agents that are biocide-tolerant or-resistant; herbicide-tolerant or -resistant; fungicide-tolerant or-resistant; pesticide-tolerant or-resistant; or tolerant or resistant to crop protection chemicals are selected or engineered. In this manner, the protection of crops from disease-causing agents or pests is enhanced.

The modified biological agents are able to grow in the presence at least one herbicide, fungicide, pesticide, or other crop protection chemical that is used in commercial farming. Such modified biological agents are able to grow and reproduce in soils where such herbicides, fungicides, pesticides, or other crop protection chemicals have been applied. The modified biological agents render the soils suppressive or resistant to disease-causing pathogens or pests. Such modified populations of biological agents can be added to soils to prevent fungal pathogens and the diseases they cause, or to inhibit feeding by insect pests or nematodes, promoting plant growth and increasing crop yield. Therefore, the present invention is useful for enhancing the competitiveness of modified biological agents particularly over other microbial agents which are not resistant to herbicides, fungicides, pesticides, or other crop protection chemicals. Therefore, compositions of the invention include selected or engineered biological agents and modified populations of biocontrol agents. These modified biological agents can be used as an inoculant or as a seed coating for plants and seeds. They can also be applied as a spray application directly to the aerial parts of plants, and can be mixed with the herbicide or other chemical to which they have been modified to become tolerant. As indicated, the presence of the modified biological agents under field conditions enhances resistance of the plants to pathogens and promotes plant growth. Such modified biological agents of the invention can be used with other agents to promote plant growth and yield.

Embodiments of the Invention Include:

1. A method for improving a biocontrol agent, said method comprising modifying said biocontrol agent to be resistant to at least one herbicide, fungicide, pesticide, or other crop protection chemical.

2. The method of embodiment 1, wherein said biocontrol agent is modified by growing in the presence of a herbicide, fungicide, pesticide, or other crop protection chemical to select a resistant strain.

3. The method of embodiment 1, wherein said biocontrol agent is modified by transforming said biocontrol agent with a gene that confers resistance to said herbicide, fungicide, pesticide, or other crop protection chemical.

4. The method of any one of embodiments 1-3, wherein said biocontrol agent is a bacterial biocontrol agent.

5. The method of any one of embodiments 1-3, wherein said biocontrol agent is selected from the group consisting of *Pseudomonas, Bacillus, Agrobacterium, Lysobacter, Trichoderma, Paecilomyces, Gliocladium, Ampelomyces, Pythium, Metschnikowia, Chromobacterium, Penicillium, Coniothyrium, Chaetomium, Myrothecium, Aureobasidium, Pantoea, Burkholderia, Streptomyces, Variovorax, Pasteuria, Lactobacillus, Paenibacillus, Xanthomonas* genera.

6. The method of embodiment 5, wherein said bacterial biocontrol agent is a *Pseudomonas* bacterium.

7. The method of embodiment 6, wherein said *Pseudomonas* is *Pseudomonas fluorescens* or *Pseudomonas chlororaphis*.

8. The method of any one of embodiments 1-7, wherein said herbicide is selected from the group consisting of glyphosate, glufosinate (glutamine synthase inhibitor), sulfonylurea and imidazolinone herbicides (branched chain amino acid synthesis inhibitors).

9. A modified biocontrol agent wherein said biocontrol agent has been selected under herbicide, fungicide, pesticide, or other crop protection chemical pressure and is resistant to said herbicide, fungicide, pesticide, or other crop protection chemical.

10. The modified biocontrol agent of embodiment 9, wherein said modified biocontrol agent is a bacterial biocontrol agent.

11. The modified biocontrol agent of embodiment 9, wherein said biocontrol agent is selected from the group consisting of *Pseudomonas, Bacillus, Agrobacterium, Lysobacter, Trichoderma, Paecilomyces, Gliocladium, Ampelomyces, Pythium, Metschnikowia, Chromobacterium, Penicillium, Coniothyrium, Chaetomium, Myrothecium, Aureobasidium, Pantoea, Burkholderia, Streptomyces, Variovorax, Pasteuria, Xanthomonas* genera.

12. The modified biocontrol agent of embodiment 10, wherein said bacterial biocontrol agent is a *Pseudomonas* bacterium.

13. The modified biocontrol agent of embodiment 12, wherein said *Pseudomonas* is *Pseudomonas fluorescens* or *Pseudomonas chlororaphis*.

14. The modified biocontrol agent of any one of embodiments 9-13, wherein said herbicide is selected from the group consisting of glyphosate, glufosinate (glutamine synthase inhibitor), sulfonylurea and imidazolinone herbicides (branched chain aminio acid synthesis inhibitors).

15. A recombinant biocontrol agent wherein said biocontrol agent has been transformed with a herbicide resistance gene rendering the biocontrol agent herbicide resistant.

16. The recombinant biocontrol agent of embodiment 15, wherein said modified biocontrol agent is a bacterial biocontrol agent.

17. The recombinant biocontrol agent of embodiment 16, wherein said bacterial biocontrol agent is selected from the group consisting of *Pseudomonas, Bacillus, Agrobacterium, Lysobacter, Gliocladium, Pythium, Chromobacterium, Penicillium, Pantoea, Burkholderia, Streptomyces, Variovorax, Pasteuria, and Xanthomonas* genera.

18. The recombinant biocontrol agent of embodiment 17, wherein said bacterial biocontrol agent is a *Pseudomonas* bacterium.

19. The recombinant biocontrol agent of embodiment 18, wherein said *Pseudomonas* is *Pseudomonas fluorescens* or *Pseudomonas chlororaphis*.

20. The recombinant biocontrol agent of any one of embodiments 15-19, wherein said herbicide is selected from the group consisting of glyphosate, glufosinate (glutamine synthase inhibitor), sulfonylurea and imidazolinone herbicides (branched chain aminio acid synthesis inhibitors).

21. A modified population of biocontrol agents wherein the population substantially comprises the biocontrol agent of any one of embodiments 1-20.

22. A formulation for controlling a plant pathogen, said formulation comprising a modified population of biocontrol agents, wherein said biocontrol agents are herbicide resistant, and a suitable carrier.

23. The formulation of embodiment 22, wherein said population comprises modified bacterial biocontrol agents.

24. The formulation of embodiment 22, wherein said population comprises recombinant biocontrol agents.

25. The formulation of any one of embodiments 22-24, wherein said biocontrol agent is present in an effective amount sufficient to improve plant health, growth or yield in the presence of an agricultural field application rate of a biocide.

26. The formulation of embodiment 25, wherein the biocontrol agent comprises the strain deposited as NRRL No. B-50897 and the biocide is glyphosate.

27. The formulation of embodiment 25, wherein the biocontrol agent comprises the strain AIP050999 deposited as NRRL No. B-50999 and the biocide is glufosinate.

28. A method for improving the ability of a biocontrol agent to compete in a field setting said method comprising modifying said biological agent such that said modified biocontrol agent is able to grow in the presence of a herbicide.

29. A method for promoting plant growth, said method comprising applying a composition comprising a modified population of biocontrol agents to the soil where said plant is growing.

30. The method of embodiment 29, wherein said biocontrol agents have been modified to be resistant to glyphosate or glufosinate.

31. A method for growing a plant comprising applying to a crop, a seed or an area of cultivation a combination of an effective amount of a biocide and an effective amount of a modified biocontrol agent wherein
  (a) the effective amount of the biocide is such as to selectively control an organism of interest while the crop is not significantly damaged; and,
  (b) the effective amount of the modified biocontrol agent is sufficient to result in a statistically significant increase in plant health, yield and/or growth when compared to the plant health, yield and/or growth that occurs when the same concentration of a non-modified biocontrol agent is applied in combination with the effective amount of the biocide.

32. The method of embodiment 31, wherein the modified biocontrol agent and the biocide are applied simultaneously.

33. The method of embodiment 32, wherein the modified biocontrol agent and the biocide are applied sequentially.

34. The method of any one of embodiments 31-33, wherein said biocontrol agent comprises the strain deposited as NRRL No. B-50897.

35. The method of embodiment 34, where the biocide is glyphosate, and wherein the effective amount of glyphosate is such as to selectively control weeds while the crop is not significantly damaged.

36. The method of any one of embodiments 31-33, wherein said biocontrol agent comprises the strain AIP050999 deposited as NRRL No. B-50999 and the biocide is glufosinate.

37. The method of embodiment 36, where the biocide is glufosinate, and wherein the effective amount of glufosinate is such as to selectively control weeds while the crop is not significantly damaged.

38. A cultured population of a biocontrol agent wherein said cultured population is produced by growing a population of agents under herbicide, fungicide, pesticide or a crop protection chemical pressure to select a purified culture of biocontrol agents that are resistant to said herbicide, fungicide, pesticide or other crop protection chemical.

39. The cultured population of the biocontrol agent of embodiment 38, wherein said biocontrol agent is present in an effective amount sufficient to improve plant health, growth or yield in the presence of an agricultural field application rate of a biocide.

40. An isolated biologically pure culture of a biocontrol agent wherein said biocontrol agent is resistant to a biocide selected from a herbicide, a fungicide, a pesticide or a crop protection chemical wherein said culture is produced by growing in the presence of said biocide.

41. The isolated biologically pure culture of the biocontrol agent of embodiment 40, wherein said biocontrol agent is present in an effective amount sufficient to improve plant health, growth or yield in the presence of an agricultural field application rate of a biocide.

42. The method of embodiment 38, wherein said composition comprises a suitable carrier.

43. A bacterial culture grown from the strain deposited as NRRL No. B-50897, wherein said bacterial culture has antifungal activity and is able to grow in the presence of glyphosate.

44. The bacterial culture of claim 43, wherein the strain deposited as NRRL No. B-50897 is present in an effective amount sufficient to improve plant health, growth or yield in the presence of an agricultural field application rate of glyphosate.

45. A bacterial culture grown from the strain AIP050999 deposited as NRRL No. B-50999, wherein said bacterial culture has antifungal activity and is able to grow in the presence of glufosinate.

46. The bacterial culture of claim 45, wherein the strain AIP050999 deposited as NRRL No. B-50999 is present in an effective amount sufficient to improve plant health, growth or yield in the presence of an agricultural field application rate of glufosinate.

47. A composition comprising at least one biological control agent comprising NRRL No. B-50999 or NRRL No. B-50897 or an active derivative thereof, wherein said biological control agent or the active derivative thereof is present at about $10^5$ CFU/gram to about $10^{11}$ CFU/gram.

48. The composition of embodiment 47, wherein said biological control agent or the active derivative thereof is present at about $10^5$ CFU/gram to about $10^{10}$ CFU/gram.

49. The composition of any one of embodiments 47-48, wherein said composition comprises a cell paste.

50. The composition of any one of embodiments 47-49, wherein said composition comprises a wettable powder.

51. The composition of any one of embodiments 47-50, wherein said composition controls a plant pathogen.

52. The composition of any one of embodiments 47-50, wherein said composition has antifungal activity.

53. The composition of embodiment 51, wherein said plant pathogen comprises a fungus. 54. The composition of embodiment 51, wherein said pathogen comprises *Phakopsora pachyrhizi* (the causal agent of Asian soybean rust).

55. A coated seed comprising a seed and a coating on said seed, wherein said coating comprises at least one biological control agent comprising NRRL No. B-50999 or NRRL No. B-50897 or an active derivative thereof.

56. The coated seed of embodiment 55, wherein said biological control agent or the active derivative thereof is present on said seed at about $10^5$ CFU/seed to about $10^7$ CFU/seed.

57. The coated seed of embodiment 55 or 56, wherein said coating further comprises at least one nutrient, at least one herbicide or at least one pesticide.

58. The coated seed of any one of embodiments 55-57, wherein said coating controls a plant pathogen.

59. The coated seed of embodiment 58, wherein the pathogen comprises a fungus.

60. The coated seed of embodiment 58, wherein said biological control agent has antifungal activity.

61. The coated seed of any one of embodiments 55-60, wherein said seed is from a monocot.

62. The coated seed of any one of embodiments 55-60, wherein said seed is from a dicot.

63. A composition comprising a cell paste comprising at least one biological control agent comprising NRRL No. B-50999 or NRRL No. B-50897 or an active derivative thereof.

64. A composition comprising a wettable power comprising at least one biological control agent comprising NRRL No. B-50999 or NRRL No. B-50897 or an active derivative thereof.

65. A method for growing a plant comprising planting in an area of cultivation a coated seed composition as set forth in any one of embodiments 55-62.

66. A method for growing a plant comprising applying to a crop or an area of cultivation an effective amount of a composition comprising at least one biological control agent comprising NRRL No. B-50999 or NRRL No. B-50897 or an active derivative thereof, wherein said effective amount comprises at least about $10^{12}$ to $10^{16}$ colony forming units (CFU) per hectare.

67. The method of embodiment 66, wherein said effective amount controls a plant pathogen.

68. The method of embodiment 67, wherein said plant pathogen comprises *Phakopsora pachyrhizi* (the causal agent of Asian soybean rust).

69. The method of embodiment 67, wherein said effective amount has antifungal activity.

70. The method of any one of embodiments 66-69, wherein said method further comprises applying an effective amount of a biocide, wherein said effective amount of the biocide selectively controls an organism of interest while the crop is not significantly damaged.

71. The method of embodiment 70, wherein the modified biocontrol agent and the biocide are applied simultaneously.

72. The method of embodiment 70, wherein the modified biocontrol agent and the biocide are applied sequentially.

73. The method of any one of embodiments 70-72, where the biocide is glyphosate, and wherein the effective amount of glyphosate is such as to selectively control weeds while the crop is not significantly damaged.

BRIEF DESCRIPTION OF FIGURES

FIG. 1 provides a growth curve of the various strains in the presence of glyphosate.

DETAILED DESCRIPTION

Compositions and methods for improving biological control agents are provided. A biological agent or biocontrol agent for purposes of the present invention is used to describe a microorganism that is used to control disease-causing plant pathogens and plant pests. The biological control agents of the invention have been modified such that they are able to grow in the presence of at least one biocide. A biocide is a chemical substance which can exert a controlling effect on an organism by chemical or biological means. Biocides include pesticides, such as fungicides; herbicides; insecticides, other crop protection chemicals, and the like. Compositions of the invention include one or more isolated biocontrol agents that has been selected for resistance to biocides such as a herbicide, fungicide, pesticide, or other crop protection chemical; a recombinant biocontrol agent that has been transformed to contain a herbicide, fungicide, pesticide, or other crop protection chemical resistant gene; a modified population of biocontrol agents wherein the population is resistant to at least one herbicide, fungicide, pesticide, or other crop protection chemical; and compositions comprising these modified populations of biocontrol agents. The modified population may comprise microorganisms that have been selected for herbicide, fungicide, pesticide, or other crop protection chemical resistance or have been transformed with a gene that confers resistance or tolerance to such herbicide, fungicide, pesticide, or other crop protection chemical. Thus, the invention comprises substantially pure cultures, or biologically pure cultures, of such modified biocontrol agents or modified biological agents. A "biologically pure bacterial culture" refers to a culture of bacteria containing no other bacterial species in quantities to be detected by normal bacteriological techniques. Stated another way, it is a culture wherein virtually all of the bacterial cells present are of the selected strain. A modified biocontrol agent includes biocontrol agents that have acquired a trait due to selection pressure and recombinant biocontrol agents that have been transformed with a gene that confers resistance or tolerance to at least one herbicide, fungicide, pesticide, or other crop protection chemical.

The invention further encompasses a particular modified biological control agent. Such agent includes AIP1620. AIP1620 is a *Pseudomonas* strain that has been selected for glyphosate tolerance. Additional agents include AIP050999. AIP050999 is a *Pseudomonas* strain that has been selected for glufosinate tolerance.

AIP1620 was deposited with the Patent Depository of the National Center for Agricultural Utilization Research Agricultural Research Service, U.S. Department of Agriculture, 1815 North University Street, Peoria, Ill. 61604 U.S.A. on Jan. 31, 2014 and assigned NRRL No. B-50897. AIP050999 was deposited with the Patent Depository of the National Center for Agricultural Utilization Research Agricultural Research Service, U.S. Department of Agriculture, 1815 North University Street, Peoria, Ill. 61604 U.S.A. on Jan. 23, 2015 and assigned NRRL No. B-50999. Each of these deposits will be maintained under the terms of the Budapest Treaty on the International Recognition of the Deposit of Microorganisms for the Purposes of Patent Procedure. This deposit was made merely as a convenience for those of skill in the art and are not an admission that a deposit is required under 35 U.S.C. § 112.

Further provided are active derivatives of NRRL No. B-50897 and NRRL No.B-50999. Some methods to identify groups of derived and functionally identical or nearly identical strains are Multi-locus sequence typing (MLST), concatenated shared genes trees. Whole Genome Alignment (WGA), and Average Nucleotide Identity (ANI). Each will be considered below. While many are also useful for higher-level groupings (species and above), the cutoffs and methodology below will be focused on those appropriate for a fine level of resolution. One approach to increasing the resolution of the rRNA gene is to use multiple genes or loci, particularly those that change more rapidly but are still universally present. There are many techniques for identifying these genes and classifying new sequences in a previous framework (see, for example, Darling, A. E., et al., (2014) *Peer J* 2:e243; Wu, M., et al., (2008) *Genome Biology* 9(10):R151; Wu, M., et al., (2012) *Bioinformatics* 28(7):1033-34; Mende, D. R., et al., (2013) *Nature Methods* 10(9):881-84; Jolley, K. A., et al., (2010) *BMC Bioinformatics* 11(1):595; and Larsen, M. V., et al., (2012) *Journal of Clinical Microbiology* 50(4):1355-61). The various references cited herein provide publically available gene sets and either set cut off values or provide methods to determine the cut off that will provide the same cut off for the same group of organisms. The larger the number of genes, the more resolution is possible, but the lack of those genes in other species make them difficult to analyze in the same framework. Cutoffs to define a group will differ based on the number and specific genes used. One extension of MLST is to use all universally shared genes (therefore the maximum possible loci) for a group of strains [for instance, as implemented in Benedict, M. N., et al., ((2014) *BMC Genomics* 15(1):8) in a concatenated shared gene alignment and inferred tree. WGA is a related series of method that aligns the entire genome sequence (not just genes or defined loci) between two or many organisms (see, for example, Angiuoli, S. V., et al., (2011) *Bioinformatics* 27(3):334-42; Darling, A. E., et al., (2010) *PLoS ONE* 5(6):e11147; and Treangen, T. J., et al., (2014) *Genome Biology* 15(11):524). For both MLST, concatenated shared gene trees, and WGA, methods exist to determine the distance between naturally occurring groups, given enough genetic information from related organism genomes (see, for example, Didelot, X., et al., (2007) *Genetics* 175(3):1251-66; and Lang, P., et al., (2010) *Applied and Environmental Microbiology* 76(6):1913-25; and Bishop, C., et al. (2009) *BMC Biology* 7(1)1741-7007-7-3.). The exact cutoffs defining each taxonomic group in a single method may vary (for instance, from 95% for rapidly changing groups to 99.7% for more slowly changing groups (Bishop, C., et al., (2009) *BMC Biology* 7(1)1741-7007-7-3.), but membership of a strain in a group is determinable using publicly available methods and will remain constant for that group. These naturally occurring groups indicate a group of closely related organisms that share an ecological function (Koeppel, A., et al., (2008) *PNAS* 105(7): 2504-9; and Cohan, F., et al., (2007) *Current Biology* 17(10): R373-86)—due to the nature of these groups, a skilled environmental microbiologist would predict that strains from the same group would be useful unless some specific change could be shown that would disrupt a particular function. Finally, ANI (see, for example, Konstantinidis, K. T., et al., (2005) *PNAS USA* 102(7):2567-72; and Richter, M., et al., (2009) *PNAS* 106(45):19126-31) and derivatives (see, for example, Varghese, N. J., et al., *Nucleic Acids Research* (Jul. 6, 2015): gkv657) are based on summarizing the average nucleotides shared between the genomes of strains that align in WGAs. While methods may differ slightly, for one widely implemented ANI method a cutoff of 99% defines a functional group (see, for example, Konstantinidis, K. T., et al., (2005) *PNAS USA* 102(7):2567-72).

By "herbicide, fungicide, pesticide, or other crop protection chemical tolerance or herbicide, fungicide, pesticide, or other crop protection chemical resistance" is intended the ability of an organism (i.e, the plant, the biocontrol agent, the biocontrol bacterial agent, etc.) to survive and reproduce following exposure to a dose of the herbicide, fungicide, pesticide, or other crop protection chemical that is normally lethal to the wild type organism.

Biological agents or biocontrol agents of the invention include microorganisms and fungi that control disease-causing plant pathogens and promote plant health, growth, and yield. Any of these biological or biocontrol agents can be modified by selection or transformation and produce a modified biological or biocontrol agent or recombinant biological or biocontrol agent. Thus, the invention encompasses an isolated modified biocontrol agent. The modified biocontrol agents can be grown to produce a population of biocontrol agents. By "modified population of biological or biocontrol agents" is intended a population of agents that substantially comprises a culture of the selected agent or the recombinant agent having the trait of interest such as resistance to a herbicide, fungicide, pesticide, or other crop protection chemical. By substantially comprises is intended that the population has been grown and produced from the modified or the recombinant biocontrol agent. That is, the modified or recombinant biocontrol agents can be grown to produce a biologically pure culture. It is recognized that such biologically pure cultures can be used together to enhance plant health, growth, or yield.

Any biological or biocontrol agent can be used in the methods of the invention. Particular microorganisms of interest include strains of the bacteria *Pseudomonas, Bacillus, Agrobacterium, Lysobacter, Gliocladium, Pythium, Chromobacterium, Penicillium, Pantoea, Lactobacillus, Paenibacillus, Burkholderia, Streptomyces, Variovorax, Pasteuria, Xanthomonas*, etc. Fungi of interest include *Aureobasidium, Ampelomyces, Beauveria, Metarhizium, Metschnikowia, Myrothecium, Lecanicillium, Chaetomium, Cordyceps, Coniothyrium, Dactylella, Gliocladium, Aspergillis, Paecilomyces, Trichoderma, Pisolithus, Glomus*, etc. See, for example, U.S. Pat. Nos. 5,348,742; 5,496,547; 5,756,087; 5,955,348; 6,060,051; 6,635,425; and U.S. Patent Publication 20130142759; all of which are herein incorporated by reference. Many biocontrol agents are on the market and any of them can be modified according to the present invention. Such agents include: *Agrobacterium radiobacter* K84; *Trichoderma atroviride; Bacillus subtilis* GB03; *Bacillus firmus* I-1582; *Trichoderma asperellum* (ICC 012); *T. gamsii* (ICC 080); *Bacillus pumilus* strain QST 2808; *Bacillus subtilis* strain QST 713; *B. subtilis* strain MBI 600; *Paecilomyces fumosoroseus; Gliocladium catenulatum; Trichoderma harzianum rifai* strain KRL-AG2; *Trichoderma harzianum* T-22; *Trichoderma harzianum* T-22; *Trichoderma virens* strain G-41; *Trichoderma harzianum* T-22; *Bacillus subtilis* QST 713; *Bacillus amyloliquefaciens* strain D747; *Trichoderma (Gliocladium) virens* GL-21; *Paecilomyces lilacinus; Paecilomyces fumosoroseus; Ampelomyces quisqualis; B. subtilis* DSM 17231; *B. licheniformis* DSM 17236; *Pythium oligandrum* DV 74; *Bacillus subtilis* GB03; *Trichoderma asperellum; T gamsii; Pseudomonas syringae* ESC-10; *Metschnikowia fructicola; Trichoderma harzianum* T-22; *Pseudomonas chlororaphis* MA 342; *B. amyloliquefaciens; Chrombacterium subtsugae* strain PRAA4-1; *B. subtilis amyloliquefaciens* FZB24; *Penicillium bilaii; Paecilomyces fumosoroseus* FE 9901; *Streptomyces lydicus* WYEC 108; *P. syringae* A506; *Coniothyrium minitans; Paecilomyces lilacinus* strain 251; *Streptomyces lydicus* WYEC-108; *Bacillus amyloliquifaciens; Trichoderma virens; Trichoderma viride; Ampelomyces quisqualis; Chaetomium globosum; Pseudomonas fluorescens; Bacillus subtilis; Bacillus pumulis; Myrothecium verrucaria* AARC-0255; *Streptomyces actinobacterium* strain K61; *Gliocladium catenulatum* J1446; *Aureobasidium pullulans* strain DSM 14940; and *A. pullulans* strain DSM 14941. Additional biological disease control products can be found on the world wide web at: nevegetable.org/table-22-biological-disease-control-products.

Disease causing pathogens include fungi, bacteria, viruses and nematodes. Biocontrol agents of the invention are those that target any of the plant pathogens. Target pathogens include but are not limited to *Alternaria, Botrytis, Fusarium, Erwinia, Pseudomonas, Xanthomonas, Cercospora, Colletotrichum, Cladosporium, -Erisyphae* spp., *Microsphaera syringae, Peronospora* spp., *Plasmopara* spp., *Phytophthora, Pythium, Rhizoctonia, Diplocarpon, Venturia, Mycosphaerella, Phomopsis, Taphrina, Elsinoe, Sclerotinia, Verticillum, Gnomonia, Fusicladium, Nectria, Phyllosticta, Diplocarpon, Albugo, Guignardia, Botrytis, Exobasidium, Entomosporium, Exobasidium, Pestalotia, Phoma, Cristulariella, Phakopsora, Thelaviopsis, Puccinia, Peronospora, Bremia, Pantoea, Clavibacter.*

In further embodiments, the modified biological agents disclosed herein (i.e., NRRL No. B-50999 or NRRL No. B-50897 or an active derivative thereof) control at least one, two or all of *Pythium, Phytophthora, or Rhizoctonia*. In further embodiments, the modified biological agents disclosed herein (i.e., NRRL No. B-50999 or NRRL No. B-50897 or an active derivative thereof) control at least one, two or all of *Pythium aphanadermatum, Phytophthora parasitica*, or *Rhizoctonnia solani*.

In other methods, the modified biological agents disclosed herein (i.e., NRRL No. B-50999 or NRRL No. B-50897 or an active derivative thereof) control *Phakopsora pachyrhizi* and/or *Botrytis cinerea*.

The terms "controlling" and "protecting a plant from a pathogen" refers to one or more of inhibiting or reducing the growth, germination, reproduction, and/or proliferation of a pathogen of interest; and/or killing, removing, destroying, or otherwise diminishing the occurrence and/or activity of a pathogen of interest. As outlined in further detail herein, in specific embodiments, the biocontrol agent controls one or more fungi (such as for example, *Pythium, Phytophthora*, and/or *Rhizoctonnia*). In further embodiments, the biocontrol agent controls *Phakopsora*. Various assays to measure such activity are disclosed elsewhere herein.

By "antipathogenic compositions" or "antipathogenic" is intended that the compositions are capable of suppressing, controlling, and/or killing the invading pathogenic organism. In specific embodiments, an antipathogenic composition reduces the disease symptoms resulting from pathogen challenge by a statistically significant amount, including for example, at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens, including, for example, *Fusarium* sp., *Phakopsora pachyrhizi, Rhizoctonia solani, Botrytis cinerea, Pythium* sp., turf pathogens, and the like.

Herbicide, fungicide, pesticide, or other crop protection chemical resistance is the ability of an organism to survive and reproduce following exposure to a dose of the herbicide, fungicide, pesticide, or other crop protection chemical that would normally be lethal to the wild type organism or would substantially reduce growth of the wild type organism. Resistance may be induced or identified due to selection or it may be induced through genetic engineering. To identify and produce a modified population of biocontrol agents through selection, the biocontrol agents are grown in the presence of the herbicide, fungicide, pesticide, or other crop protection chemical as the selection pressure. Susceptible agents are killed while resistant agents survive to reproduce without competition. As the biocontrol agents are grown in the presence of the herbicide, fungicide, pesticide, or other crop protection chemical, resistant biocontrol agents successfully reproduce and become dominant in the population, becoming a modified population of biocontrol agents. Methods for selecting resistant strains are known and include U.S. Pat. Nos. 4,306,027 and 4,094,097, herein incorporated by reference. Therefore, the invention includes a biologically pure culture of a resistant biocontrol strain. The resistant strains of the invention have the same identification characteristics as the original sensitive strain except they are significantly more tolerant to the particular herbicide, fungicide, pesticide, or other crop protection chemical. Thus, their identification is readily possible by comparison with characteristics of the known sensitive strain.

Herbicides include glyphosate, ACCase inhibitors (Aryloxyphenoxy propionate (FOPS)); ALS inhibitors (Sulfonylurea (SU)), Imidazonlinone (IMI), Pyrimidines (PM)); microtubule protein inhibitor (Dinitroaniline (DNA)); synthetic auxins (Phenoxy (P)), Benzoic Acid (BA), Carboxylic acid (CA)); Photosystem II inhibitor (Triazine (TZ)), Triazinone (TN), Nitriles (NT), Benzothiadiazinones (BZ), Ureas (US)); EPSP Synthase inhibitor (glycines (GC)); Glutamine Synthesis inhibitor (Phosphinic Acid (PA)); DOXP synthase inhibitor (Isoxazolidinone (IA)); HPPD inhibitor (Pyrazole (PA)), Triketone (TE)); PPO inhibitors (Diphenylether (DE), N-phenylphthalimide (NP) (Ary triazinone (AT)); VLFA inhibitors (chloroacetamide (CA)), Oxyacetamide (OA)); Photosystem I inhibitor (Bipyridyliums (BP)); and the like.

Pesticides include imidacloprid clothianidin, arylpyrazole compounds (WO2007103076); organophosphates, phenyl pyrazole, pyrethoids caramoyloximes, pyrazoles, amidines, halogenated hydrocarbons, carbamates and derivatives thereof, terbufos, chloropyrifos, fipronil, chlorethoxyfos, telfuthrin, carbofuran, imidacloprid, tebupirimfos (U.S. Pat. No. 5,849,320).

Fungicides include aliphatic nitrogen fungicides (butylamine, cymoxanil, dodicin, dodine, guazatine, iminoctadine); amide fungicides (benzovindiflupyr, carpropamid, chloraniformethan, cyflufenamid, diclocymet, diclocymet, dimoxystrobin, fenaminstrobin, fenoxanil, flumetover, furametpyr, isofetamid, isopyrazam, mandestrobin, mandipropamid, metominostrobin, orysastrobin, penthiopyrad, prochloraz, quinazamid, silthiofam, triforine); acylamino acid fungicides (benalaxyl, benalaxyl-M, furalaxyl, metalaxyl, metalaxyl-M, pefurazoate, valifenalate); anilide fungicides (benalaxyl, benalaxyl-M, bixafen, boscalid, carboxin, fenhexamid, fluxapyroxad, isotianil, metalaxyl, metalaxyl-M, metsulfovax, ofurace, oxadixyl, oxycarboxin, penflufen, pyracarbolid, sedaxane, thifluzamide, tiadinil, vanguard); benzanilide fungicides (benodanil, flutolanil, mebenil, mepronil, salicylanilide, tecloftalam); furanilide fungicides (fenfuram, furalaxyl, furcarbanil, methfuroxam); sulfonanilide fungicides (flusulfamide); benzamide fungicides (benzohydroxamic acid, fluopicolide, fluopyram, tioxymid, trichlamide, zarilamid, zoxamide); furamide fungicides (cyclafuramid, furmecyclox); phenylsulfamide fungicides (dichlofluanid, tolylfluanid); sulfonamide fungicides (amisulbrom, cyazofamid); valinamide fungicides (benthiavalicarb, iprovalicarb); antibiotic fungicides (aureofungin, blasticidin-S, cycloheximide, griseofulvin, kasugamycin, moroxydine, natamycin, polyoxins, polyoxorim, streptomycin, validamycin); strobilurin fungicides (fluoxastrobin, mandestrobin); methoxyacrylate strobilurin fungicides (azoxystrobin, bifujunzhi, coumoxystrobin, enoxastrobin, flufenoxystrobin, jiaxiangjunzhi, picoxystrobin, pyraoxystrobin); methoxycarbanilate strobilurin fungicides (pyraclostrobin, pyrametostrobin, triclopyricarb); methoxyiminoacetamide strobilurin fungicides (dimoxystrobin, fenaminstrobin, metominostrobin, orysastrobin); methoxyiminoacetate strobilurin fungicides (kresoxim-methyl, trifloxystrobin); aromatic fungicides (biphenyl, chlorodinitronaphthalenes, chloroneb, chlorothalonil, cresol, dicloran, fenjuntong, hexachlorobenzene, pentachlorophenol, quintozene, sodium pentachlorophenoxide, tecnazene, trichlorotrinitrobenzenes); arsenical fungicides (asomate, urbacide); aryl phenyl ketone fungicides (metrafenone, pyriofenone); benzimidazole fungicides (albendazole, benomyl, carbendazim, chlorfenazole, cypendazole, debacarb, fuberidazole, mecarbinzid, rabenzazole, thiabendazole); benzimidazole precursor fungicides (furophanate, thiophanate, thiophanate-methyl); benzothiazole fungicides (bentaluron, benthiavalicarb, benthiazole, chlobenthiazone, probenazole); botanical fungicides (allicin, berberine, carvacrol, carvone, osthol, sanguinarine, santonin); bridged diphenyl fungicides (bithionol, dichlorophen, diphenylamine, hexachlorophene, parinol); carbamate fungicides (benthiavalicarb, furophanate, iodocarb, iprovalicarb, picarbutrazox, propamocarb, pyribencarb, thiophanate, thiophanate-methyl, tolprocarb); benzimidazolylcarbamate fungicides (albendazole, benomyl, carbendazim, cypendazole, debacarb, mecarbinzid); carbanilate fungicides (diethofencarb, pyraclostrobin, pyrametostrobin, triclopyricarb); conazole fungicides, conazole fungicides (imidazoles) (climbazole, clotrimazole, imazalil, oxpoconazole, prochloraz, triflumizole); conazole fungicides (triazoles) (azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, uniconazole-P); copper fungicides (acypetacs-copper, Bordeaux mixture, Burgundy mixture, Cheshunt mixture, copper acetate, copper carbonate, basic, copper hydroxide, copper naphthenate, copper oleate, copper oxychloride, copper silicate, copper sulfate, copper sulfate, basic, copper zinc chromate, cufraneb, cuprobam, cuprous oxide, mancopper, oxine-copper, saisentong, thiodiazole-copper); cyanoacrylate fungicides (benzamacril, phenamacril); dicarboximide fungicides (famoxadone, fluoroimide); dichlorophenyl dicarboximide fungicides (chlozolinate, dichlozoline, iprodione, isovaledione, myclozolin, procymidone, vinclozolin); phthalimide fungicides (captafol, captan, ditalimfos, folpet, thiochlorfenphim); dinitrophenol fungicides (binapacryl, dinobuton, dinocap, dinocap-4, dinocap-6, meptyldinocap, dinocton, dinopenton, dinosulfon, dinoterbon, DNOC); dithiocarbamate fungicides (amobam, asomate, azithiram, carbamorph, cufraneb, cuprobam, disulfiram, ferbam, metam, nabam, tecoram, thiram, urbacide, ziram); cyclic dithiocarbamate fungicides (dazomet, etem, milneb); polymeric dithiocarbamate fungicides (mancopper, mancozeb, maneb, metiram, polycarbamate, propineb, zineb); dithiolane fungicides (isoprothiolane, saijunmao); fumigant fungicides (carbon disulfide, cyanogen, dithioether, methyl bromide, methyl iodide, sodium tetrathiocarbonate); hydrazide fungicides (benquinox, saijunmao); imidazole fungicides (cyazofamid, fenamidone, fenapanil, glyodin, iprodione, isovaledione, pefurazoate, triazoxide); conazole fungicides (imidazoles) (climb azole, clotrimazole, imazalil, oxpoconazole, prochloraz, triflumizole); inorganic fungicides (potassium azide, potassium thiocyanate, sodium azide, sulfur, see also copper fungicides, see also inorganic mercury fungicides); mercury fungicides; inorganic mercury fungicides (mercuric chloride, mercuric oxide, mercurous chloride); organomercury fungicides ((3-ethoxypropyl)mercury bromide, ethylmercury acetate, ethylmercury bromide, ethylmercury chloride, ethylmercury 2,3-dihydroxypropyl mercaptide, ethylmercury phosphate, N-(ethylmercury)-p-toluenesulphonanilide, hydrargaphen, 2-methoxyethylmercury chloride, methylmercury benzoate, methylmercury dicyandiamide, methylmercury pentachlorophenoxide, 8-phenylmercurioxyquinoline, phenylmercuriurea, phenylmercury acetate, phenylmercury chloride, phenylmercury derivative of pyrocatechol, phenylmercury nitrate, phenylmercury salicylate, thiomersal, tolylmercury acetate); morpholine fungicides (aldimorph, benzamorf, carbamorph, dimethomorph, dodemorph, fenpropimorph, flumorph, tridemorph); organophosphorus fungicides (ampropylfos, ditalimfos, EBP, edifenphos, fosetyl, hexylthiofos, inezin, iprobenfos, izopamfos, kejunlin, phosdiphen, pyrazophos, tolclofos-methyl, triamiphos); organotin fungicides (decafentin, fentin, tributyltin oxide); oxathiin fungicides (carboxin, oxycarboxin); oxazole fungicides (chlozolinate, dichlozoline, drazoxolon, famoxadone, hymexazol, metazoxolon, myclozolin, oxadixyl, oxathiapiprolin, pyrisoxazole, vinclozolin); polysulfide fungicides (barium polysulfide, calcium polysulfide, potassium polysulfide, sodium polysulfide); pyrazole fungicides (benzovindiflupyr, bixafen, fenpyrazamine, fluxapyroxad, furametpyr, isopyrazam, oxathiapiprolin, penflufen, penthiopyrad, pyraclostrobin, pyrametostrobin, pyraoxystrobin, rabenzazole, sedaxane); pyridine fungicides (boscalid, buthiobate, dipyrithione, fluazinam, fluopicolide, fluopyram, parinol, picarbutrazox, pyribencarb, pyridinitril, pyrifenox, pyrisoxazole, pyroxychlor, pyroxyfur, triclopyricarb); pyrimidine fungicides (bupirimate, diflumetorim, dimethirimol, ethirimol, fenarimol, ferimzone, nuarimol, triarimol); anilinopyrimidine fungicides (cyprodinil, mepanipyrim, pyrimethanil); pyrrole fungicides (dimetachlone, fenpiclonil, fludioxonil, fluoroimide); quaternary ammonium fungicides (berberine, sanguinarine); quinoline fungicides (ethoxyquin, halacrinate, 8-hydroxyquinoline sulfate, quinacetol, quinoxyfen, tebufloquin); quinone fungicides (chloranil, dichlone, dithianon); quinoxaline fungicides (chinomethionat, chlorquinox, thioquinox); thiadiazole fungicides (etridiazole, saisentong, thiodiazole-copper, zinc thiazole); thiazole fungicides (ethaboxam, isotianil, metsulfovax, octhilinone, oxathiapiprolin, thiabendazole, thifluzamide); thiazolidine fungicides (flutianil, thiadifluor); thiocarbamate fungicides (methasulfocarb, prothiocarb); thiophene fungicides (ethaboxam, isofetamid, silthiofam); triazine fungicides (anilazine); triazole fungicides (amisulbrom, bitertanol, fluotrimazole, triazbutil); conazole fungicides (triazoles) (azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, huanjunzuo, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, uniconazole-P); triazolopyrimidine fungicides (ametoctradin); urea fungicides (bentaluron, pencycuron, quinazamid); zinc fungicides (acypetacs-zinc, copper zinc chromate, cufraneb, mancozeb, metiram, polycarbamate, polyoxorim-zinc, propineb, zinc naphthenate, zinc thiazole, zinc trichlorophenoxide, zineb, ziram); unclassified fungicides (acibenzolar, acypetacs, allyl alcohol, benzalkonium chloride, bethoxazin, bromothalonil, chitosan, chloropicrin, DBCP, dehydroacetic acid, diclomezine, diethyl pyrocarbonate, ethylicin, fenaminosulf, fenitropan, fenpropidin, formaldehyde, furfural, hexachlorobutadiene, methyl isothiocyanate, nitrostyrene, nitrothal-isopropyl, OCH, pentachlorophenyl laurate, 2-phenylphenol, phthalide, piperalin, propamidine, proquinazid, pyroquilon, sodium orthophenylphenoxide, spiroxamine, sultropen, thicyofen, tricyclazole) or mefenoxam.

As indicated, recombinant biocontrol agents having resistance to a herbicide, fungicide, pesticide, or other crop protection chemical can be made through genetic engineering techniques and such engineered or recombinant biocontrol agents grown to produce a modified population of biocontrol agents. A recombinant biocontrol agent is produced by introducing polynucleotides into the biocontrol host cell by transformation. Methods for transforming microorganisms are known and available in the art. See, generally, Hanahan, D. (1983) Studies on transformation of *Escherichia coli* with plasmids *J. Mol. Biol.* 166,557-77; Seidman, C. E. (1994) In: *Current Protocols in Molecular Biology*, Ausubel, F. M. et al. eds., John Wiley and Sons, N.Y.; Choi et al. (2006) J. Microbiol. Methods 64:391-397; Wang et al. 2010. *J. Chem. Technol. Biotechnol.* 85:775-778. Transformation may occur by natural uptake of naked DNA by competent cells from their environment in the laboratory. Alternatively, cells can be made competent by exposure to divalent cations under cold conditions, by electroporation, by exposure to polyethylene glycol, by treatment with fibrous nanoparticles, or other methods well known in the art.

Herbicide resistance genes for use in transforming a recombinant biocontrol agent include, but are not limited to, fumonisin detoxification genes (U.S. Pat. No. 5,792,931); acetolactate synthase (ALS) mutants that lead to herbicide resistance, in particular the sulfonylurea-type herbicides, such as the S4 and/or Hra mutations; inhibitors of glutamine synthase such as phosphinothricin or basta (e.g., bar gene); and glyphosate resistance (EPSPS gene)); and HPPD resistance (WO 96/38576, U.S. Pat. Nos. 6,758,044; 7,250,561; 7,935,869; and 8,124,846), or other such genes known in the art. The disclosures of which are herein incorporated by reference. The bar gene encodes resistance to the herbicide basta, the nptII gene encodes resistance to the antibiotics kanamycin and geneticin, and the ALS-gene mutants encode resistance to the sulfonylurea herbicides including chlorsulfuron, metsulfuron, sulfometuron, nicosulfuron, rimsulfuron, flazasulfuron, sulfosulfuron, and triasulfuron, and the imadizolinone herbicides including imazethapyr, imazaquin, imazapyr, and imazamethabenz.

The modified populations of biological control agents of the invention can be formulated as a cell paste, wettable powders, dusts, granules, aqueous or oil based liquid products, and the like. Such formulations will comprise the modified biological control agents in addition to carriers and other agents. The formulations can be used as field inoculants for biocontrol, seed coatings, etc. That is, the modified biocontrol populations can be used in any manner known in the art, including coating seeds with an effective amount of the modified agents, in furrow application of the modified biocontrol populations directly into the soil, in foliar application, mixing into a potting mixture, and in post-harvest disease control. Such methods are known in the art and are described, for example, in U.S. Pat. No. 5,348,742 and in published European Application EP0472494 A2, both of which are herein incorporated by reference. Biocontrol includes management of resident populations of organisms and introductions of specific organisms to reduce disease.

The various compositions and the various formulations disclosed herein can comprise a biological control agent, such as NRRL No. B-50999 or NRRL No. B-50897 or an active derivative thereof, in an effective amount. Such an effective amount can comprise a concentration of the biological control agent of at least about $10^5$ CFU/gram to about $10^{11}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, about $10^{11}$ CFU/gram to about $10^{12}$ CFU/gram. In other embodiments, the concentration of the biological control agent comprises at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram. Such concentrations of the biological control agents can occur in any formulation type of interest, including, for example in a wettable power or in a cell paste.

Cell pastes and wettable powers can comprise a biological control agent, such as NRRL No. B-50999 or NRRL No. B-50897 or an active derivative thereof, in an effective amount. Such an effective amount can comprise a concentration of the biological control agent of at least about $10^5$ CFU/gram to about $10^{11}$ CFU/gram, about $10^7$ CFU/gram to about $10^{10}$ CFU/gram, about $10^7$ CFU/gram to about $10^{11}$ CFU/gram, about $10^6$ CFU/gram to about $10^{10}$ CFU/gram, about $10^6$ CFU/gram to about $10^{11}$ CFU/gram, about $10^{11}$ CFU/gram to about $10^{12}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{11}$ CFU/gram to about $10^{11}$ CFU/gram, about $10^{11}$ CFU/gram to about $10^{12}$ CFU/gram. In other embodiments, the concentration of the biological control agent comprises at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram, at least about $10^{13}$ CFU/gram.

Further provided is a coated seed which comprises a seed and a coating on the seed, wherein the coating comprises at least one biological control agent, such as NRRL No. B-50999 or NRRL No. B-50897 or an active derivative thereof, wherein said biological control agent or the active derivative thereof is present on the seed at about $10^5$ CFU/seed to about $10^7$ CFU/seed, at about $10^4$ CFU/seed to about $10^8$ CFU/seed, at about $10^4$ CFU/seed to about $10^5$ CFU/seed, at about $10^5$ CFU/seed to about $10^6$ CFU/seed, at about $10^6$ CFU/seed to about $10^7$ CFU/seed, at about $10^7$ CFU/seed to about $10^8$ CFU/seed. The seed coating can be applied to any seed of interest (i.e., for a monocot or a dicot). Various plants of interest are disclosed elsewhere herein.

A seed coating can further comprise at least at least one nutrient, at least one herbicide or at least one pesticide, or at least one biocide. See, for example, US App Pub. 20040336049, 20140173979, and 20150033811.

The biocontrol agent provided herein can be mixed with a fungicide, insecticide, or herbicide to enhance its activity or the activity of the chemical to which it has been added. In some cases the combination of the biocontrol agent and chemical may show synergistic activity, where the mixture of the two exceeds that expected from their simple additive effect.

The modified biological control agents of the invention can be used to significantly reduce disease, to promote plant growth and yield, and to reduce reliance on traditional pesticides. The modified agents of the invention can be used with other pesticides for an effective integrated pest management program. In one embodiment, the modified biocontrol populations can be mixed in formulation with known pesticides in a manner described in WO 94/10845, herein incorporated by reference.

The modified biocontrol populations are applied in an effective amount. An effective amount of a modified biocontrol population is an amount sufficient to control or inhibit the pathogen. In other embodiments, the effective amount of the modified biocontrol agent is an amount sufficient to promote or increase plant health, growth or yield in the presence of an agricultural field application rate of a biocide. The rate of application of the modified biocontrol agent and/or the biocide may vary according to the pathogen being targeted, the crop to be protected, the efficacy of the modified biocontrol populations, the severity of the disease, the climate conditions, and the like. Generally for a field inoculation, the rate of modified biocontrol agent application is $10^{12}$ to $10^{16}$ colony forming units (CFU) per hectare. (This corresponds to about 10 g to 10 kg of active ingredient per hectare if the a.i. is 100 billion CFU per g.). In other embodiments, for a field inoculation, the rate of modified biocontrol agent application is $3 \times 10^{15}$ to $1 \times 10^{17}$ colony forming units (CFU) per hectare. (This corresponds to about 30 kg to 1000 kg of active ingredient per hectare if the a.i. is 100 billion CFU per g.). In other embodiments, for a field inoculation, the rate of modified biocontrol agent application is $3 \times 10^{15}$ to $1 \times 10^{17}$ colony forming units (CFU) per hectare; about $1 \times 10^{12}$ to about $1 \times 10^{13}$ colony forming units (CFU) per hectare, about $1 \times 10^{13}$ to about $1 \times 10^{14}$ colony forming units (CFU) per hectare, about $1 \times 10^{14}$ to about $1 \times 10^{15}$ colony forming units (CFU) per hectare, about $1 \times 10^{15}$ to about $1 \times 10^{16}$ colony forming units (CFU) per hectare or about $1 \times 10^{16}$ to about $1 \times 10^{17}$ colony forming units (CFU) per hectare. In other embodiments, for a field inoculation, the rate of modified biocontrol agent application is at least about $1 \times 10^{13}$, about $1 \times 10^{14}$, $1 \times 10^{15}$, about $1 \times 10^{16}$ or about $1 \times 10^{17}$ colony forming units (CFU) per hectare. In still other embodiments, the rate of modified biocontrol agent application is 10 g to 50 kg, 50 kg to 100 kg, 100 kg to 200 kg, 200 kg to 300 kg, 300 kg to 400 kg, 400 kg, to 500 kg, 500 kg to 600 kg, 600 kg to 700 kg, 700 kg to 800 kg, 800 kg to 900 kg, 900 kg to 1000 kg of active ingredient per hectare if the a.i. is 100 billion CFU per g. In still other embodiments, the rate of modified biocontrol agent application is at least 10 g, 50 kg, 100 kg, 200 kg, 300 kg, 400 kg, 500 kg, 600 kg, 700 kg, 800 kg, 900 kg, 1000 kg of active ingredient per hectare if the a.i. is 100 billion CFU per g. In specific embodiments, the modified biocontrol agent applied comprises the strain deposited as NRRL No. B-50897 and/or the strain AIP050999 deposited as NRRL No. B-50999.

Any appropriate agricultural application rate for a biocide can be applied to the crop, for example, an effective amount of the biocide that controls a given organism (i.e., a pest of interest, such as fungus, insects, weeds, disease, ect) may be applied. Methods to assay for the effective amount of the modified biocontrol agent include, for example, any statistically significant increase in plant health, yield and/or growth that occurs upon application of an effective amount of the biocontrol agent and a field application rate of a biocide when compared to the plant health, yield and/or growth that occurs when the same concentration of a non-modified biocontrol agent is applied in combination with the effective amount of the biocide.

Therefore, a further embodiment of the invention provides a method for controlling or inhibiting the growth of a plant pathogen by applying the population of modified biological control agents of the invention to an environment in which the plant pathogen may grow. The application may be to the plant, to parts of the plant, to the seeds of the plants to be protected, or to the soil in which the plant to be protected are growing or will grow. Application to the plant or plant parts may be before or after harvest. Application to the seeds will be prior to planting of the seeds.

Thus, a method for growing a plant is provided and comprises planting in an area of cultivation a coated seed as described elsewhere herein. In specific embodiments, the seed is coated with NRRL No. B-50999 or NRRL No. B-50897 or an active derivative thereof. Various concentrations of CFUs per seed are disclosed elsewhere herein. Further provided is a method for growing a plant comprising applying to a crop or an area of cultivation an effective amount of a composition comprising at least one biological control agent comprising NRRL No. B-50999 or NRRL No. B-50897 or an active derivative thereof. Various effective amounts of biological control agent are disclosed elsewhere herein and in one, non-limiting example, the effective amount of the biological control agent comprises at least about $10^{12}$ to $10^{16}$ colony forming units (CFU) per hectare.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc.), a greenhouse, a growth chamber, etc.

In other embodiments, a crop, area of cultivation, seed and/or weed can be treated with a combination an effective amount of the modified control agent and an effective amount of a biocide. By "treated with a combination of" or "applying a combination of" modified biocontrol agent and a biocide to a crop, area of cultivation or field it is intended that one or more of a particular field, plant crop, seed and/or weed is treated with one or more of the modified biocontrol agent and one or more biocide so that a desired effect is achieved. Furthermore, the application of one or both of the modified biocontrol agent and the biocide can occur prior to the planting of the crop (for example, to the soil, the seed, or the plant). Moreover, the application of the modified biocontrol agent and the biocide may be simultaneous or the applications may be at different times (sequential), so long as the desired effect is achieved.

In one non-limiting embodiment, the modified biocontrol agent is resistant to glyphosate and further increases plant health, yield or growth when applied in an effective amount, and the biocide comprises glyphosate or an active derivative thereof. In such methods, a seed, plant or area of cultivation is treated with a combination of an effective amount of the modified biocontrol agent that is resistant to glyphosate and an effective amount of glyphosate, wherein the effective amount of glyphosate is such as to selectively control weeds while the crop is not significantly damaged. In such embodiments, the effective amount of the modified biocontrol agent is sufficient to result in a statistically significant increase in plant health, yield and/or growth when compared to the plant health, yield and/or growth that occurs when the same concentration of a non-modified biocontrol agent is applied in combination with the effective amount of the glyphosate or active derivative thereof. In a further embodiment, the biocontrol agent comprises an effective amount of AIP1620.

In another one non-limiting embodiment, the modified biocontrol agent is resistant to glufosinate and further increases plant health, yield or growth when applied in an effective amount, and the biocide comprises glufosinate or an active derivative thereof. In such methods, a seed, plant or area of cultivation is treated with a combination of an effective amount of the modified biocontrol agent that is resistant to glufosinate and an effective amount of glufosinate, wherein the effective amount of glufosinate is such as to selectively control weeds while the crop is not significantly damaged. In such embodiments, the effective amount of the modified biocontrol agent is sufficient to result in a statistically significant increase in plant health, yield and/or growth when compared to the plant health, yield and/or growth that occurs when the same concentration of a non-modified biocontrol agent is applied in combination with the effective amount of the glufosinate or active derivative thereof. In a further embodiment, the biocontrol agent comprises an effective amount of AIP050999.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The modified biocontrol agent can be employed with any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentals*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), butter beans, kidney beans (*Phaseolus vulgaris*), cowpeas (*Vigna unguiculata*), pigeon peas (*Cajanus cajan*), yam beans, jicama, a legumes, peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, a corn or soybean plants is employed.

The following examples are offered by way of illustration and not by way of limitation.

EXPERIMENTAL

Example 1

Production of Glyphosate Resistant Mutants of AIP0069

Introduction

Biological agents are now being used in agriculture to reduce risk and improve yield. One important attribute of these biological agents is that they must be compatible with chemicals that may also be applied in commercial farming practice. Glyphosate is a chemical herbicide that accounts for about 25% of the global herbicide market and is applied at a rate of around 200 million pounds per year. This herbicide inhibits the enzyme, 5-enolpyruvylshikimate-3-phosphate (EPSP) synthase (EPSPS) which catalyzes one step in aromatic amino acid biosynthesis in plants and many bacteria. Thus glyphosate decreases viability of organisms including any biocontrol agents that rely on EPSPS, and it has been reported to alter the plant microbial community. This report describes successful introduction of glyphosate tolerance into a *Pseudomonas fluorescens* strain used in biological control of several important fungal plant pathogens, including Pythium and Rhizoctonia, the causal agents in the agriculturally important "Damping Off" disease complex. In addition to improving chemical compatibility of this biocontrol agent, introduction of glyphosate resistance offers additional advantages in commercial production.

In addition to the example of glyphosate provided here, other agricultural chemicals may inhibit the growth of desirable biological control or plant growth promoting bacteria. Examples include the herbicides glufosinate (glutamine synthase inhibitor), sulfonylurea and imidazolinone herbicides (branched chain aminio acid synthesis inhibitors) and the antibiotics streptomycin, oxytetracycline and kasugamycin.

Materials and Methods and Results

The biological control strain *Pseudomonas fluorescens* AIP0069 was streaked onto agar plates containing 0 or 5 mM glyphosate. The basal medium consisted of 11.3 g $Na_2HPO_4 \cdot 7H_2O$, 3 g $KH_2PO_4$, 1 g $NH_4Cl$, 10 g monosodium glutamate, 31 g molasses, 493 mg $MgSO_4.7H_2O$, 50 mg $ZnSO_4 \cdot 7H_2O$, 5 mg $FeSO_4 \cdot 7H_2O$, and 0.3 g thiamine per liter of deionized water. In the absence of glyphosate numerous bacterial colonies were visible after incubating overnight at 25 C. In the presence of 5 mM glyphosate no colonies were visible after a similar incubation, however, after extended incubation of several days a few colonies were seen. These colonies were isolated and grown in liquid medium at multiple glyphosate concentrations. One isolate, named GlyphR1, was ten-fold more resistant to glyphosate than the parent AIP0069 strain (FIG. 1). This improved strain is expected to be more competitive, and thus more effective as a biocontrol, than AIP0069 or similar glyphosate-sensitive strains in agricultural systems where glyphosate is present in the soil and crops. Also, glyphosate can be used as a selective agent during the production, formulation and/or storage of this strain to prevent contamination by other bacteria.

Example 2

Biological Control Activity of Glyphosate Resistant Mutants

Bacteria were inoculated into 50 ml of broth medium consisting of 11.3 g $Na_2HPO_4 \cdot 7H_2O$, 3 g $KH_2PO_4$, 1 g $NH_4Cl$, 10 g Monosodium glutamate, 30 g molasses, 493 mg $MgSO_4 \cdot 7H_2O$, 50 mg $ZnSO_4 \cdot 7H_2O$, and 5 mg $FeSO_4 \cdot 7H_2O$ per liter of deionized water. Cultures were grown in 250 ml baffled flasks in a shaking incubator at 28 C, 250 rpm for 2 days. Cells were collected by centrifugation at 3500×g for 10 minutes. The culture supernatants were discarded and the cells were resuspended in sterile deionized water to the volumes of the original cultures. AIP0323, a mutant of AIP0069 which does not have antifungal activity, was included as a negative control.

*Rhizoctonia solani* infested rice grain was produced as described previously (K. A. Holmes and D. M. Benson, 1994 Evaluation of Phytophthora parasitica var. nicotianae as a biocontrol for Phytophthora parasitica on Catharanthus roseus. Plant Disease 78:193-199.) Infested rice was pulverized in a blender and screened through a #10 sieve (2 mm opening). The pulverized grain was mixed with germination medium at the rate of 2 g per liter.

Impatiens seeds were planted into the infested germination medium in size 402 plug trays, treated with 0.3 ml of resuspended bacteria per plug and grown under standard greenhouse production conditions. There were 2 replicates for each experimental treatment with 20 plugs per replicate. The number of healthy seedlings was assessed after two weeks. The data below in Table 1 demonstrate that the glyphosate resistant variants AIP0404 and AIP1620 retain full antifungal activity, compared to the progenitor strain, AIP0069.

TABLE 1

| Treatment | % healthy seedlings | | |
|---|---|---|---|
| | Replicate 1 | Replicate 2 | Average |
| Noninoculated control | 90 | 90 | 90 |
| Inoculated control | 15 | 20 | 17.5 |
| Inoculated + AIP0069 | 75 | 80 | 77.5 |
| Inoculated + AIP0323 | 10 | 15 | 12.5 |
| Inoculated + AIP0404 | 75 | 80 | 77.5 |
| Inoculated + AIP1620 | 80 | 75 | 77.5 |

The biocontrol strain can be used to control Fusarium head blight, Asian Soybean Rust, *Rhizoctonia, Botrytis, Pythium*, turf diseases, and the like.

Example 3

Genes encoding glyphosate tolerant EPSPS enzymes may be obtained from various bacteria (A. Schulz et al, 1985. Differential sensitivity of bacterial 5-enolpyruvylshikimate-3-phosphate synthases to the herbicide glyphosate. FEMS Microbiology Letters, 28:297-301). In particular, the EPSPS genes from *Agrobacterium tumefaciens* CP4 (G. F. Barry et al, 1992. Inhibitors of amino acid biosynthesis: Strategies for imparting glyphosate tolerance to crop plants. p. 139-145. In B. K. Singh et al. (e.) Biosynthesis and molecular regulation of amino acids in plants. Am. Soc. Plant Physiologists, Rockville, Md.), and *Arthrobacter globiformis* (C. L. Peters et al, 2010, GRG23 and GRG51 genes conferring herbicide resistance. U.S. Pat. No. 7,674,958), are highly resistant.

A suitable gene is amplified by PCR or made synthetically using techniques well known in the art. The open reading frame is cloned into the plasmid vector pKK223-3 (Pharmacia) between the tacI promoter and the rrnB transcriptional terminator. The tacI promoter provides strong constitutive expression of genes in *Pseudomonas*. Genomic DNA sequences from strain AIP0069 are incorporated on each side of the promoter—gene—terminator cassette to direct homologous recombination into the AIP0069 chromosome.

The resulting plasmid is mobilized from *E. coli* to *Pseudomonas fluorescens* AIP0069 by conjugation, a technique well known in the art, and selection on defined medium containing 100 mM glyphosate. The plasmid contains the narrow host range colE1 origin of replication and thus cannot replicate in *Pseudomonas*. Glyphosate resistant colonies will be obtained when the promoter—gene—terminator cassette integrates into the *Pseudomonas* chromosome by homologous recombination. Single crossover events (where the entire plasmid is integrated into the chromosome) are distinguished from double crossover events (where only the desired promoter—gene—terminator cassette is integrated) by PCR, Southern blotting, or other techniques well known in the art. A double crossover event is selected for use.

Example 4

AIP1620 starter cultures were inoculated using colonies from Luria agar plates and grown in 0.1X NBY broth (0.8 g of Difco Nutrient Broth powder and 0.5 g of yeast extract powder per liter of deionized water) and grown at 28 C, 250 rpm. Production cultures were grown in a broth containing, per liter of deionized water: 11.3 g $Na_2HPO_4 \cdot 7H_2O$, 3.0 g $KH_2PO_4$, 1.0 g $NH_4Cl$, 10 g monosodium glutamate, 3.0 g molasses, 0.49 g $MgSO_4 \cdot 7H_2O$, 50 mg $ZnSO_4 \cdot 7H_2O$, 5 mg $FeSO_4 \cdot 7H_2O$ and sufficient hydrochloric acid to adjust the pH to approximately 6.2. Fifty ml of production broth was placed in a 250 ml baffled culture flask, inoculated with 0.5 ml of starter culture and incubated at 28 C, 250 rpm. The production cultures were inoculated at various times and then harvested simultaneously to yield cultures with incubation times of 15, 24, 33, and 43 hours. Forty ml of each culture was harvested by centrifugation. The spent culture broth was discarded and the cells were re-suspended in autoclaved deionized water to 40 ml final volume.

Fungal inoculum was prepared using the rice grain method described by Holmes and Benson (K. A. Holmes and D. M. Benson, 1994. Evaluation of *Phytophthora parasitica* var. *nicotianae* for biocontrol of *Phytophthora parasitica* on *Catharanthus roseus*. Plant Disease, 78:193-199.). Infested rice grains were pulverized in a blender and screened through a #10 sieve. This inoculum was mixed into Fafard superfine germinating mix at the rate of 1.0 g per liter.

The inoculated germination mix was placed in 392 greenhouse plug trays (Landmark Plastic Corporation, Akron, Ohio) and one impatiens seed was planted into each cell. AIP1620 cell suspensions were applied at the rate of 0.3 ml per cell. The seeds were germinated under standard greenhouse conditions. There were 3 replicates of each treatment with 20 cells per replicate. After 10 to 14 days the assays were scored by counting the number of healthy seedlings in each treatment. Results are summarized in Table 2 below.

TABLE 2

Performance AIP1620 cells in greenhouse seed germination assay

| Treatment | Culture time | Live seedlings (out of 20) | |
|---|---|---|---|
| | | Mean | Standard deviation |
| Non-inoculated control | n/a | 15.0 | 0.0 |
| Inoculated control | n/a | 2.7 | 1.2 |
| AIP1620 | 15 hrs | 6.3 | 1.2 |
| AIP1620 | 24 hrs | 13.3 | 4.6 |
| AIP1620 | 33 hrs | 15.0 | 0.0 |
| AIP1620 | 44 hrs | 14.7 | 2.5 |

Example 5

Multiple greenhouse trials of AIP1620 cells were performed over a 10 month period. For each trial AIP1620 cultures were grown, harvested and re-suspended in autoclaved deionized water essentially as described in Example 4 using a culture time of approximately 24 hours. The greenhouse germination trials also were performed as described in Example 4, but the *R. solani* inoculum rate varied from 0.25 to 1.0 g of pulverized rice grain per liter of germination mix, depending on the trial. The results compiled from 17 trials are shown in Table 3 below and demonstrate consistent performance of AIP1620 in controlling damping off disease.

TABLE 3

Performance AIP1620 cells in multiple greenhouse seed germination assays

| | Live seedlings (out of 20) | | | | | |
|---|---|---|---|---|---|---|
| | Non-inoculated Control | | Inoculated Control | | Inoculated plus AIP1620 | |
| Trial | Mean | SD | Mean | SD | Mean | SD |
| 1 | 17.0 | 1.0 | 1.3 | 0.6 | 11.3 | 2.5 |
| 2 | 17.3 | 2.5 | 9.0 | 1.0 | 17.3 | 2.1 |
| 3 | 14.0 | 0.0 | 2.0 | 1.0 | 16.7 | 2.3 |
| 4 | 12.3 | 1.5 | 1.7 | 1.5 | 13.3 | 3.1 |
| 5 | 18.4 | 1.1 | 3.8 | 1.8 | 16.8 | 1.3 |
| 6 | 16.4 | 1.7 | 2.6 | 2.1 | 13.6 | 2.5 |
| 7 | 16.6 | 1.1 | 2.8 | 1.3 | 15.8 | 1.3 |
| 8 | 19.7 | 0.6 | 3.0 | 1.0 | 17.3 | 0.6 |
| 9 | 19.0 | 1.0 | 3.7 | 1.5 | 15.7 | 1.2 |
| 10 | 16.3 | 0.6 | 1.7 | 2.1 | 15.7 | 0.6 |
| 11 | 18.5 | 0.7 | 2.0 | 0.0 | 14.5 | 0.7 |
| 12 | 18.0 | 1.0 | 3.0 | 3.0 | 16.3 | 0.6 |
| 13 | 18.8 | 1.9 | 3.8 | 2.1 | 17.0 | 0.8 |
| 14 | 17.0 | 0.0 | 3.5 | 0.7 | 15.5 | 0.7 |
| 15 | 18.6 | 1.1 | 4.8 | 1.3 | 14.8 | 2.8 |
| 16 | 19.5 | 0.6 | 3.5 | 2.5 | 18.5 | 1.5 |
| 17 | 18.0 | 0.0 | 1.0 | 1.7 | 15.3 | 0.6 |

Example 6

Fifty grams of AIP1620 cell paste was mixed with 50 g of Min-U-Gel 400 or Min-U-Gel 200 attapulgite clay (Active Minerals International, LLC, Sparks, Md.) dried to a water activity of less than 0.3. One portion of each formulation was stored at 4° C. and another was stored at 22° C. The viability of these formulations was tested at various times by dilution plating and the results are shown in Table 4 below. After 21 days in storage, the samples which had been stored at 4° C. were tested in a greenhouse seed germination assay and found to have retained antifungal activity against Rhizoctonia solani.

TABLE 4

Survival of formulated AIP1620 cells during storage at 4° C. or 22° C.

| Formulation | Colony forming units per gram of AIP1620 after storage for | | |
|---|---|---|---|
| | 2 weeks | 4 weeks | 20 weeks |
| Min-U-Gel 400 stored at 22° C. | $5.4 \times 10^7$ | $2.0 \times 10^6$ | $<2.0 \times 10^4$ |
| Min-U-Gel 400 stored at 4° C. | $1.3 \times 10^8$ | $3.5 \times 10^8$ | Not tested |
| Min-U-Gel 200 stored at 22° C. | $8.2 \times 10^8$ | $3.7 \times 10^8$ | $7.2 \times 10^5$ |
| Min-U-Gel 200 stored at 4° C. | $1.8 \times 10^{10}$ | $9.0 \times 10^9$ | Not tested |

Example 7

One hundred grams of AIP1620 cell paste was mixed with 20 g of synthetic calcium silicate (MicroCel E, Imerys Filtration Minerals, Lompoc, Calif.) using a food processor. The resulting material contained $2.7 \times 10^{10}$ colony forming units per gram (CFU/g) of AIP1620, as determined by dilution plating. This material was dried at 40 C to a water activity of less than 0.30 at which time it contained $1.4 \times 10^9$ CFU/g of AIP1620. The dried powder formulation was stored in vacuum sealed mylar pouches at 22 C. After 85 days the powder contained $1.1 \times 10^6$ CFU/g of AIP1620 and retained antifungal activity against *Rhizoctonia solani* as determined by a greenhouse seed germination assay.

Example 8

One hundred grams of AIP1620 cell paste was mixed with 5 g of glycerol and 20 g of synthetic calcium silicate using a food processor. The resulting material contained $5.7 \times 10^{11}$ CFU/g of AIP1620, as determined by dilution plating. This material was dried at 40 C to a water activity of less than 0.30 at which time it contained $3.1 \times 10^9$ CFU/g of AIP1620. The dried powder formulation was stored in vacuum sealed mylar pouches at 22 C. After 61 days the powder contained $6.2 \times 10^8$ CFU/g of AIP1620 and retained antifungal activity against *Rhizoctonia solani as* determined by a greenhouse seed germination assay.

Example 9

One hundred grams of AIP1620 cell paste was mixed with 5 g of trehalose and 20 g of synthetic calcium silicate using a food processor. The resulting material contained $5.7 \times 10^{11}$ CFU/g of AIP1620, as determined by dilution plating. This material was dried at 40 C to a water activity of less than 0.30 at which time it contained $4.0 \times 10^8$ CFU/g of AIP1620. The dried powder formulation was stored in vacuum sealed mylar pouches at 22 C. After 54 days the powder contained $2.7 \times 10^7$ CFU/g of AIP1620.

Example 10

Four grams of xanthan gum and was dispersed into 4 g of soybean oil. The resulting mixture was combined with 100 g of AIP1620 cell paste and allowed to thicken for about 5 minutes at room temperature. The thickened mixture was blended into 20 g of synthetic calcium silicate using a food processor. The resulting material contained $9.4 \times 10^{11}$ CFU/g of AIP1620 and was divided into two 50 g portions. One portion was dried at 40 C to a water activity of <0.30 at which time it contained $7.0 \times 10^8$ CFU/g of AIP1620.

The other portion was dried over silica gel at room temperature to a water activity of <0.10 at which time it contained $1.18 \times 10^{10}$ CFU/g of AIP1620.

Example 11

Five different formulations were prepared essentially as described in Example 4, above, using the excipients and proportions shown in Table 5, below. These formulations were dried at 40° C. to a water activity of less than 0.30 and stored at 4° C.

Fungal inoculum was prepared using the rice grain method described by Holmes and Benson (K. A. Holmes and D. M. Benson, 1994. Evaluation of *Phytophthora parasitica* var. *nicotianae* for biocontrol of *Phytophthora parasitica* on *Catharanthus roseus*. Plant Disease, 78:193-199.). Infested rice grains were pulverized in a blender and screened through a #10 sieve. This inoculum was mixed into Fafard superfine germinating mix at the rate of 0.25 g per liter.

The inoculated mix was divided and formulated AIP1620 was added at the rate of 5 g per liter. Impatiens seed were planted into the inoculated and treated mixes. The seeds were germinated under standard greenhouse conditions. After 10 days the assays were scored by counting the number of healthy seedlings in each treatment. Results are summarized in Table 6 below.

TABLE 5

Composition of formulations

| Formula-tion | AIP1620 cell paste | Excipient | Final water activity |
|---|---|---|---|
| A | 50 g | 50 g Minugel 400 attapulgite clay | 0.29 |
| B | 50 g | 50 g Minugel 200 attapulgite clay | 0.28 |
| C | 50 g | 50 g Agsorb 325 RVM attapulgite clay | 0.24 |
| D | 100 g | 15 g Sipernat 22S hydrophilic silica | 0.26 |
| E | 100 g | 15 g Aerosil 200F silica | 0.29 |

TABLE 6

Performance of formulated AIP1620 in greenhouse seed germination assay

| | | Live seedlings (out of 20) | |
|---|---|---|---|
| Treatment | Storage time | Mean | Standard deviation |
| Non-inoculated control | n/a | 19.7 | 0.6 |
| Inoculated control | n/a | 3.0 | 1.0 |
| Formulation A | 45 days | 12.7 | 4.9 |
| Formulation B | 45 days | 9.0 | 6.2 |
| Formulation C | 45 days | 17.3 | 1.2 |
| Formulation D | 45 days | 17.3 | 0.6 |
| Formulation F | 45 days | 11.7 | 2.1 |

Example 12

Several formulations were prepared as described in Examples 4 through 8, above, at different times. The composition of the different formulations is shown in Table 7, below. After drying to a water activity of 0.30 or lower, the formulated materials were vacuum sealed into mylar pouches and stored at 22° C.

Fungal inoculum was prepared using the rice grain method described by Holmes and Benson (K. A. Holmes and D. M. Benson, 1994. Evaluation of *Phytophthora parasitica* var. *nicotianae* for biocontrol of *Phytophthora parasitica* on *Catharanthus roseus*. Plant Disease, 78:193-199.). Infested rice grains were pulverized in a blender and screened through a #10 sieve. This inoculum was mixed into Fafard superfine germinating mix at the rate of 0.25 g per liter.

The inoculated mix was divided and formulated AIP1620 was added at the rate of 5 g per liter. On the same day, a subsample of each formulation was dilution plated to determine the CFU/g of AIP1620. Impatiens seed were planted into the inoculated and treated mixes. The seeds were germinated under standard greenhouse conditions. After 10 to 14 days the assays were scored by counting the number of healthy seedlings in each treatment. Results are summarized in Table 8 below.

TABLE 7

| Composition of formulations | | | | |
|---|---|---|---|---|
| Formulation | AIP1620 cell paste | Additions | Excipient | Drying method |
| F | 100 g | None | 20 g calcium silicate | 40° C. oven |
| G | 100 g | 5 g glycerol | 20 g calcium silicate | 40° C. oven |
| H | 100 g | none | 50 g MinuGel 200 | 40° C. oven |
| I | 100 g | 4 g xanthan gum, 4 g soybean oil | 20 g calcium silicate | Room temp, silica gel |
| J | 100 g | 4 g xanthan gum, 4 g soybean oil | 20 g calcium silicate | 40° C. oven |
| K | 100 g | 4 g xanthan gum, 4 g olive oil | 20 g calcium silicate | 40° C. oven |

TABLE 8

| Performance of formulated AIP1620 in greenhouse seed germination assay | | | | |
|---|---|---|---|---|
| | | CFU | Live seedlings (out of 20) | |
| Treatment | Storage time | AIP1620 per g | Mean | Standard deviation |
| Non-inoculated control | n/a | | 18.3 | 0.6 |
| Inoculated control | n/a | | 2.3 | 3.2 |
| Formulation F | 12 days | $5.2 \times 10^6$ | 5.7 | 2.5 |
| Formulation G | 12 days | $8.3 \times 10^6$ | 10.3 | 3.2 |
| Formulation F | 18 days | $8.0 \times 10^5$ | 16.7 | 1.5 |
| Formulation G | 18 days | $3.4 \times 10^9$ | 16.7 | 1.1 |
| Formulation H | 25 days | $5.7 \times 10^9$ | 4.7 | 0.7 |
| Formulation I | 39 days | $7.7 \times 10^9$ | 16.7 | 1.5 |
| Formulation J | 39 days | $1.3 \times 10^7$ | 8.0 | 1.7 |
| Formulation K | 39 days | $3.6 \times 10^8$ | 5.3 | 1.5 |

These results demonstrate that formulated AIP1620 retains viability and activity, that is, the ability to protect seedlings against damping off disease.

Example 13

Fifty grams of AIP1620 cell paste was mixed with 50 g of Min-U-Gel 400 or Min-U-Gel 200 attapulgite clay (Active Minerals International, LLC, Sparks, Md.) dried to a water activity of less than 0.2, and stored at 22 C. The viability of these formulations was tested at various times by dilution plating and the results are shown in Table 9 below. After 21 days both formulations were tested in a greenhouse seed germination assay and found to have retained antifungal activity against *Rhizoctonia solani*.

TABLE 9

| | Colony forming units per gram of AIP1620 after storage at 22° C. for | | |
|---|---|---|---|
| Formulation | 14 days | 30 days | 141 days |
| A: Min-U-Gel 400 | $1.3 \times 10^6$ | $3.5 \times 10^6$ | $<2.0 \times 10^4$ |
| B: Min-U-Gel 200 | $1.8 \times 10^8$ | $9.0 \times 10^7$ | $7.2 \times 10^5$ |

Example 14

Greenhouse experiments were performed to demonstrate the efficacy of AIP1620 in controlling *Botrytis cinerea*.

AIP1620 starter cultures were inoculated using colonies from Luria agar plates and grown in 0.1×NBY broth (0.8 g of Difco Nutrient Broth powder and 0.5 g of yeast extract powder per liter of deionized water) and grown at 28 C, 250 rpm. Production cultures were grown in a broth containing, per liter of deionized water: 11.3 g $Na_2HPO_4 \cdot 7H_2O$, 3.0 g $KH_2PO_4$, 1.0 g $NH_4Cl$, 10 g monosodium glutamate, 3.0 g molasses, 0.49 g $MgSO_4 \cdot 7H_2O$, 50 mg $ZnSO_4 \cdot 7H_2O$, 5 mg $FeSO_4 \cdot 7H_2O$ and sufficient hydrochloric acid to adjust the pH to approximately 6.2. Fifty ml of production broth was placed in a 250 ml baffled culture flask, inoculated with 0.5 ml of starter culture and incubated at 28 C, 250 rpm. The production cultures were inoculated at various times and then harvested simultaneously to yield cultures with incubation times of 15, 24, 33, and 43 hours. Forty ml of each culture was harvested by centrifugation. The spent culture broth was discarded and the cells were re-suspended in autoclaved deionized water to 40 ml final volume.

*Botrytis cinerea* was grown on potato dextrose broth for 1 to 2 weeks without shaking. The resulting mycelial mat was removed from the broth and homogenized in autoclaved deionized water to produce liquid inoculum.

Organically grown strawberries were purchased at a local market. The unblemished fruits were selected and dipped into the *B. cinerea* inoculum for 2 to 3 seconds, then allowed to dry for 60 minutes before treatment. AIP1620 treatments were applied by dipping the inoculated fruits into the cell suspension for 2-3 seconds. The fruit were then placed into sealed plastic containers with moist paper towels to maintain high humidity and stored at room temperature for 72 to 84 hours. There were 14 replicates (berries) in each treatment. Each berry was rated on a visual spoilage severity scale of 0=no damage, 1=25%, 2=50% damage, 3=75% damage, and 4=100% (i.e., complete coverage of the berry by the fungus). Results are summarized in Table 10 below.

TABLE 10

| Postharvest control of Grey Mold of strawberries by AIP1620 cells | |
|---|---|
| Treatment | Average spoilage severity rating |
| Non-inoculated control | 3.1 |
| Inoculated control | 3.3 |
| Inoculated plus AIP1620 | 0.7 |

Example 15

Greenhouse experiments were performed to demonstrate the efficacy of AIP1620 in controlling damping off disease caused by the oomycete plant pathogen *Pythium aphanadermatum*.

AIP1620 starter cultures were inoculated using colonies from Luria agar plates and grown in 0.1×NBY broth (0.8 g of Difco Nutrient Broth powder and 0.5 g of yeast extract powder per liter of deionized water) and grown at 28 C, 250 rpm. Production cultures were grown in a broth containing, per liter of deionized water: 11.3 g $Na_2HPO_4 \cdot 7H_2O$, 3.0 g $KH_2PO_4$, 1.0 g $NH_4Cl$, 10 g monosodium glutamate, 3.0 g molasses, 0.49 g $MgSO_4 \cdot 7H_2O$, 50 mg $ZnSO_4 \cdot 7H_2O$, 5 mg $FeSO_4 \cdot 7H_2O$ and sufficient hydrochloric acid to adjust the pH to approximately 6.2. Fifty ml of production broth was placed in a 250 ml baffled culture flask, inoculated with 0.5 ml of starter culture and incubated at 28 C, 250 rpm. The production cultures were inoculated at various times and then harvested simultaneously to yield cultures with incubation times of 15, 24, 33, and 43 hours. Forty ml of each culture was harvested by centrifugation. The spent culture broth was discarded and the cells were re-suspended in autoclaved deionized water to 40 ml final volume.

Inoculum of *P. aphanadermatum* was prepared using the rice grain method described by Holmes and Benson (K. A. Holmes and D. M. Benson, 1994. Evaluation of *Phytophthora parasitica* var. *nicotianae* for biocontrol of *Phytophthora parasitica* on *Catharanthus roseus*. Plant Disease, 78:193-199.). Infested rice grains were pulverized in a blender and screened through a #10 sieve. This inoculum was mixed into Fafard superfine germinating mix at the rate of 6.0 g per liter (trials 1-4) or 7.0 g per liter (trial 5).

The inoculated germination mix was placed in 392 greenhouse plug trays (Landmark Plastic Corporation, Akron, Ohio) and one impatiens seed was planted into each cell. AIP1620 cell suspensions were applied at the rate of 0.3 ml per cell. The seeds were germinated under standard greenhouse conditions. There were 2 or 3 replicates of each treatment with 20 cells per replicate. After 7 to 17 days the assays were scored by counting the number of healthy seedlings in each treatment. Results are summarized in Table 11 below.

TABLE 11

Control of *Pythium* damping off disease by AIP1620 cells in a greenhouse seed germination assay. Values are mean +/− standard deviation.

| | Live seedlings (out of 20) | | | | |
|---|---|---|---|---|---|
| Treatment | Trial 1 | Trial 2 | Trial 3 | Trial 4 | Trial 5 |
| Non-inoculated control | 18.0 ± 1.4 | 18.5 ± 0.7 | 17.5 ± 0.7 | 16.5 ± 0.7 | 17.3 ± 0.0 |
| Inoculated control | 12.0 ± 0.0 | 10.5 ± 0.7 | 9.0 ± 1.4 | 8.5 ± 0.7 | 10.7 ± 0.7 |
| Inoculated plus AIP1620 | 17.0 ± 1.4 | 15.5 ± 2.1 | 13.5 ± 2.1 | 12.5 ± 0.7 | 16.3 ± 0.7 |

Example 16

Control of Asian Soybean Rust with AIP1620

AIP1620 cells were produced as described in the previous examples. *Phakopsora pachyrhizi* was grown on susceptible soybean plants and ureidinospores were harvested by vacuum suction from infected leaves which manifested erupted pustules (Twizeyimana, M., and Hartman, G. L. 2010. Culturing Phakopsora pachyrhizi on detached leaves and urediniospore survival at different temperatures and relative humidities. Plant Disease 94:1453-1460).

Williams 82 soybean plants were grown in plant growth chambers using techniques well known in the art. When plants were at V3-stage, the first fully expanded trifoliate leaf was sprayed with re-suspended AIP1620 cells, a chemical fungicide standard, or deionized water (inoculated control). One day later the leaves were inoculated with a suspension of *P. pachyrhizi* ureidinospores ($1 \times 10^5$/ml). Both inoculation and strain/fungicide were applied using an atomizer attached to an air compressor. The plants were maintained in a growth chamber at 95% RH with a daily cycle of 12 h of light and 12 h of darkness at 21 and 23° C., respectively. After two weeks disease severity was scored by counting the number of sporulating uredinia in randomly selected 1 cm diameter circles on the inoculated leaves. There were 3 replications (plants) for each treatment and 3 uredinia counts for each replication. The results are shown in table 12, below and demonstrate that applications of AIP1620 effectively control Asian Soybean Rust disease caused by *Phakopsora pachyrhizi*.

TABLE 12

| Treatment | Sporulating uredinia per 1-cm diameter circle |
|---|---|
| Inoculated control | 22.1 |
| Chemical standard | 0.0 |
| AIP1620 | 1.8 |

Example 17

AIP1620 Compatibility with Commercial Fungicides

The viability of AIP1620 was measured after mixing the strain 3 commercial fungicides, each containing a different active ingredient (Table 13). Fungicide concentrations were selected to simulate those in a typical tank mix for field application.

AIP1620 was grown in 3 mL of LB medium in a 10 mL tube for 24 hours at 28° C., 250 rpm. Cell pellets were harvested by centrifugation and suspended in 3 mL of $dH_2O$. Nine hundred microliters of cell suspension was mixed with 100 microliters of 10× fungicide stock and incubated at 28° C. for 5 minutes or 120 minutes.

TABLE 13

| Formulated chemical fungicides | | |
|---|---|---|
| Brand Name | Active ingredient | Volume of product per 100 mL |
| Quadris | Azoxystrobin | 936 µL |
| Spectator Ultra 1.3 | Propiconazole | 1.87 mL |
| Subdue Maxx | Mefenoxam | 78.1 µL |

After incubation with the fungicides the cells were harvested by centrifugation as described above, re-suspended in deionized water. Aliquots were serially diluted in deionized water, plated on LB agar and incubated at 28 C for 2 days using techniques well known in the art. Bacterial colonies were counted and the number of colony forming units per ml (CFU/ml) in the original solutions were calculated. The data are shown in Table 14 below and demonstrate that the viability of AIP 1620 is not adversely affected by mixing with these formulated fungicides.

TABLE 14

Viability of AIP1620 cells after incubation with fungicide formulations in a simulated tank mix.

| Fungicide | CFU/mL after incubation time | |
|---|---|---|
| | 5 Minutes | 120 Minutes |
| Water (control) | $3.70 \times 10^9$ | $8.67 \times 10^8$ |
| Quadris | $4.50 \times 10^9$ | $4.87 \times 10^9$ |
| Spectator | $2.33 \times 10^9$ | $2.17 \times 10^9$ |
| Subdue | $4.67 \times 10^9$ | $3.63 \times 10^9$ |

Example 18

Evaluation of the Protectant Activity of Mixtures of AIP1620 and Fungicides Against Asian Soybean Rust Caused by *Phakopsora pachyrhizi*

Bacteria are inoculated into 50 ml of broth medium consisting of 11.3 g $Na_2HPO_4 \cdot 7H_2O$, 3 g $KH_2PO_4$, 1 g $NH_4Cl$, 10 g Monosodium glutamate, 30 g molasses, 493 mg $MgSO_4 \cdot 7H_2O$, 50 mg $ZnSO_4 \cdot 7H_2O$, and 5 mg $FeSO_4 \cdot 7H_2O$ per liter of deionized water. Cultures are grown in 250 ml baffled flasks in a shaking incubator at 28 C, 250 rpm for 2 days. Cells are collected by centrifugation at 3500 xg for 10 minutes. The culture supernatants are discarded and the cells are re-suspended in sterile deionized water to the volumes of the original cultures. AIP0323, a mutant of AIP0069 which does not have antifungal activity, is included as a negative control.

Ureidinospores of Phakopsora pachyrhizi are harvested by vacuum suction from leaves infected with the fungus that manifest erupted pustules. The spores are re-suspended in water at 10^5/mL and inoculated onto detached soybean leaves as an aerosol using an airbrush using techniques known in the art (Twizeyimana, M., and Hartman, G. L. 2010. Culturing Phakopsora pachyrhizi on detached leaves and urediniospore survival at different temperatures and relative humidities. Plant Disease 94:1453-1460).

Mixtures of AIP1620 cells re-suspended in water and fungicidal active ingredients are prepared in various ratios comprising 10^6, 10^7, 10^8, 10^9 or 10^10 AIP1620 cells/mL, mixed with fungicidal active ingredient at 1/10×, 1/3×, 1/2×, or 1× normal field use rate, calculated by converting the field rate from the published label to g/mL, based on an assumption about spray volume per hectare or acre.

The inoculated soybean leaves are treated the biocontrol agent at the titers above, and with the fungicides at the rates above, as well as with mixtures of biocontrol agent and fungicide in various combinations at the titers and rates specified above. In addition, some inoculated detached leaves are left untreated, or treated with AIP0323 as controls. At least 3 leaves (or leaf segments) are used for each treatment of biocontrol agent, chemical, or mixture. The detached leaves are incubated in high humidity in a growth chamber on a 12 light, 21° C./12 hour dark, 23° C. After 10-14 days, the leaves are observed and scored according to the number of visible uredinia/cm^2.

Colby's equation is used to determine the fungicidal effects expected from the mixtures. (See Colby, S. R., Calculation of the synergistic and antagonistic response of herbicide combinations. Weeds 1967, 15, 20-22, herein incorporated by reference in its entirety.)

The following equation is used to calculate the expected activity of mixtures containing two active ingredients, A and B:

Expected=A−B−(A×B/100)

A=observed efficacy of active component A at the same concentration as used in the mixture;

B=observed efficacy of active component B at the same concentration as used in the mixture.

Representative synergistic interactions, including application rates employed and resulting disease control are observed and recorded as follows:

% DC=Percent disease control
% DC Obs=Percent disease control observed
% DC Exp=Percent disease control expected
Synergism factor=% DC Obs/% DC Exp Example 19

Selection of a Population of the Biological Control Strain *Pseudomonas fluorescens* AIP000069 that has Acquired Resistance to the Herbicide Glufosinate 50 microliters of AIP000069 culture, grown in 0.5× LB for 24 hours at 28° C., was spread onto plates containing M63 Plus medium with 0 or 100 mM Glufosinate. The M63 Plus medium consisted of 13.6 g $KH_2PO_4$, 9.92 g $C_6H_{12}O_6$, 2 g $(NH_4)_2SO_4$, 5.5 mg $CaCl_2$, 0.278 mg $FeSO_4 \cdot 7H_2O$, and 10.16 mg $MgCl_2 \cdot 6H_2O$ per liter of deionized water. In the absence of Glufosinate numerous bacterial colonies (a lawn) were visible after incubating plates for 2 days at 28° C. In the presence of 100 mM Glufosinate no colonies were visible after a similar incubation, however, after extended incubation of several days a single colony grew. This colony was streaked to isolation on an M63 agar plate containing 100 mM Glufosinate. The resulting isolate was named AIP050999. Growth of AIP050999 was compared to the parent strain, AIP000069, and a glyphosate resistant version of the strain AIP001620. Results are summarized in the table 15 below.

TABLE 15

Growth of strains on M63 Plus agar medium in the presence and absence of glufosinate.

| Strain | 0 mM Glufosinate | 100 mM Glufosinate |
|---|---|---|
| AIP000069 | +++ | − |
| AIP001620 | +++ | − |
| AIP050999 | +++ | +++ |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A composition comprising a biological control agent and tebuconazole, wherein said biological control agent is deposited as NRRL No. B-50897 and is a viable *Pseudomonas chlororaphis* strain, wherein said biological control agent and said tebuconazole are provided in an amount effective to control a plant pathogen.

2. The composition of claim 1, wherein the pathogen is a fungus.

3. A seed coated with the composition of claim 1.

4. A method of controlling a plant pathogen comprising applying to a crop, a seed, or an area of cultivation a biological control agent and tebuconazole, wherein said biological control agent is deposited as NRRL No. B-50897 and is a viable *Pseudomonas chlororaphis* strain, wherein said biological control agent and said tebuconazole are provided in an amount effective to control a plant pathogen.

5. The method of claim 4, wherein said biological control agent and said tebuconazole are applied simultaneously.

6. The method of claim 4, wherein said biological control agent and said tebuconazole are applied sequentially.

7. The method of claim 4, wherein said plant is a monocot.

8. The method of claim 4, wherein said plant is a dicot.

9. The method of claim 4, wherein the pathogen is a fungus.

* * * * *